United States Patent
Huang

(10) Patent No.: US 10,858,656 B2
(45) Date of Patent: Dec. 8, 2020

(54) KRAS NUCLEIC ACIDS AND USES THEREOF

(71) Applicant: AVIDITY BIOSCIENCES, INC., La Jolla, CA (US)

(72) Inventor: Hanhua Huang, San Diego, CA (US)

(73) Assignee: AVIDITY BIOSCIENCES, INC., La Jolla, CA (US)

( * ) Notice: Subject to any disclaimer, the term of this patent is extended or adjusted under 35 U.S.C. 154(b) by 0 days.

(21) Appl. No.: 15/476,102

(22) Filed: Mar. 31, 2017

(65) Prior Publication Data

US 2017/0283806 A1    Oct. 5, 2017

Related U.S. Application Data

(60) Provisional application No. 62/316,937, filed on Apr. 1, 2016.

(51) Int. Cl.
*C12N 15/11* (2006.01)
*C12N 15/113* (2010.01)

(52) U.S. Cl.
CPC ...... *C12N 15/1137* (2013.01); *C12N 15/1135* (2013.01); *C12N 2310/11* (2013.01); *C12N 2310/14* (2013.01); *C12N 2310/31* (2013.01); *C12N 2310/313* (2013.01); *C12N 2310/315* (2013.01); *C12N 2310/321* (2013.01); *C12N 2310/3231* (2013.01)

(58) Field of Classification Search
CPC .............. C12N 15/113; C12N 15/1135; C12N 2310/11; C12N 2310/114; C12N 2310/315; C12N 2310/321
USPC ................................. 536/23.1, 24.5; 514/44
See application file for complete search history.

(56) References Cited

U.S. PATENT DOCUMENTS

| | | |
|---|---|---|
| 5,142,047 A | 8/1992 | Summerton et al. |
| 5,185,444 A | 2/1993 | Summerton et al. |
| 5,334,711 A | 8/1994 | Sproat et al. |
| 5,610,052 A | 3/1997 | Thompson et al. |
| 5,716,824 A | 2/1998 | Beigelman et al. |
| 5,889,136 A | 3/1999 | Scaringe et al. |
| 5,898,031 A | 4/1999 | Crooke |
| 6,008,400 A | 12/1999 | Scaringe et al. |
| 6,107,094 A | 8/2000 | Crooke |
| 6,111,086 A | 8/2000 | Scaringe |
| 7,056,704 B2 | 6/2006 | Tuschl et al. |
| 7,078,196 B2 | 7/2006 | Tuschl et al. |

(Continued)

FOREIGN PATENT DOCUMENTS

| | | |
|---|---|---|
| EP | 1144623 B1 | 8/2002 |
| EP | 0928290 B1 | 3/2005 |

(Continued)

OTHER PUBLICATIONS

Allerson et al. (J. Med. Chem. 2005 vol. 48:901-904).*

(Continued)

*Primary Examiner* — Terra C Gibbs
(74) *Attorney, Agent, or Firm* — Wilson Sonsini Goodrich & Rosati

(57) ABSTRACT

Disclosed herein are molecules and pharmaceutical compositions that mediate RNA interference against KRAS. Also described herein include methods for treating a disease or disorder that comprises a molecule or a pharmaceutical composition that mediate RNA interference against KRAS.

17 Claims, 1 Drawing Sheet
Specification includes a Sequence Listing.

(56) References Cited

U.S. PATENT DOCUMENTS

| | | | |
|---|---|---|---|
| 7,432,249 B2 | 10/2008 | Crooke | |
| 7,432,250 B2 | 10/2008 | Crooke | |
| 7,459,547 B2 | 12/2008 | Zamore et al. | |
| 7,629,321 B2 | 12/2009 | Crooke | |
| 7,732,593 B2 | 6/2010 | Zamore et al. | |
| 7,750,144 B2 | 7/2010 | Zamore et al. | |
| 7,772,203 B2 | 8/2010 | Zamore et al. | |
| 7,786,290 B2 | 8/2010 | Woppmann et al. | |
| 7,829,693 B2 | 11/2010 | Kreutzer et al. | |
| 7,850,975 B2 | 12/2010 | Mullis | |
| 7,928,217 B2 | 4/2011 | Vornlocher et al. | |
| 8,202,979 B2 | 6/2012 | McSwiggen et al. | |
| 8,268,986 B2 | 9/2012 | Beigelman et al. | |
| 8,273,866 B2 | 9/2012 | McSwiggen et al. | |
| 8,283,329 B2 | 10/2012 | Fire et al. | |
| 8,304,530 B2 | 11/2012 | Zamore et al. | |
| 8,309,704 B2 | 11/2012 | Zamore et al. | |
| 8,309,705 B2 | 11/2012 | Zamore et al. | |
| 8,329,892 B2 | 12/2012 | Zamore et al. | |
| 8,334,373 B2 | 12/2012 | Vornlocher et al. | |
| 8,362,231 B2 | 1/2013 | Tuschl et al. | |
| 8,372,968 B2 | 2/2013 | Tuschl et al. | |
| 8,420,391 B2 | 4/2013 | Tuschl et al. | |
| 8,445,237 B2 | 5/2013 | Tuschl et al. | |
| 8,546,143 B2 | 10/2013 | Kreutzer et al. | |
| 8,552,171 B2 | 10/2013 | Tuschl et al. | |
| 8,591,910 B2 | 11/2013 | Mullis | |
| 8,604,184 B2 | 12/2013 | Mullis et al. | |
| 8,632,997 B2 | 1/2014 | Tuschl et al. | |
| 8,648,185 B2 | 2/2014 | McSwigen et al. | |
| 8,691,786 B2 | 4/2014 | Rossi et al. | |
| 8,765,930 B2 | 7/2014 | Tuschl et al. | |
| 8,772,469 B2 | 7/2014 | Uhlmann et al. | |
| 8,778,902 B2 | 7/2014 | Tuschl et al. | |
| 8,790,922 B2 | 7/2014 | Tuschl et al. | |
| 8,796,016 B2 | 8/2014 | Tuschl et al. | |
| 8,796,443 B2 | 8/2014 | Khvorova et al. | |
| 8,846,894 B2 | 9/2014 | McSwiggen et al. | |
| 8,853,384 B2 | 10/2014 | Tuschl et al. | |
| 8,895,718 B2 | 11/2014 | Tuschl et al. | |
| 8,895,721 B2 | 11/2014 | Tuschl et al. | |
| 8,933,044 B2 | 1/2015 | Tuschl et al. | |
| 8,993,745 B2 | 3/2015 | Tuschl et al. | |
| 9,012,138 B2 | 4/2015 | Tuschl et al. | |
| 9,012,621 B2 | 4/2015 | Tuschl et al. | |
| 9,096,636 B2 | 8/2015 | Baker et al. | |
| 9,175,289 B2 | 11/2015 | Khvorova et al. | |
| 9,193,753 B2 | 11/2015 | Tuschl et al. | |
| 9,212,364 B2 | 12/2015 | Sah et al. | |
| 9,284,551 B2 | 3/2016 | Puri et al. | |
| 2002/0142980 A1 | 10/2002 | Thompson et al. | |
| 2003/0143732 A1* | 7/2003 | Fosnaugh | C12N 15/113 435/325 |
| 2004/0121348 A1 | 6/2004 | Kreutzer et al. | |
| 2005/0176018 A1 | 8/2005 | Thompson et al. | |
| 2010/0055783 A1 | 3/2010 | Quay et al. | |
| 2011/0021604 A1 | 1/2011 | Brown | |
| 2011/0039914 A1 | 2/2011 | Pavco et al. | |
| 2011/0263680 A1 | 10/2011 | Khvorova et al. | |
| 2013/0045520 A1 | 2/2013 | Woolf et al. | |
| 2013/0164366 A1 | 6/2013 | Kreutzer et al. | |
| 2013/0177631 A1 | 7/2013 | Kreutzer et al. | |
| 2014/0194610 A1 | 7/2014 | Verdine et al. | |
| 2014/0288158 A1 | 9/2014 | Rajeev et al. | |
| 2014/0357700 A1 | 12/2014 | Rossi et al. | |
| 2015/0038554 A1 | 2/2015 | Brown | |
| 2015/0038555 A1 | 2/2015 | Brown | |
| 2015/0141492 A1 | 5/2015 | Tuschl et al. | |
| 2015/0211006 A1 | 7/2015 | Butler et al. | |
| 2016/0030332 A1 | 2/2016 | Lee et al. | |
| 2016/0032288 A1 | 2/2016 | Tuschl et al. | |

FOREIGN PATENT DOCUMENTS

| | | | |
|---|---|---|---|
| EP | 1214945 B1 | 6/2005 | |
| EP | 1579015 A2 | 9/2005 | |
| EP | 1352061 B1 | 5/2006 | |
| EP | 1742958 A2 | 1/2007 | |
| EP | 1407044 B1 | 9/2007 | |
| EP | 1550719 B1 | 12/2008 | |
| EP | 1349927 B1 | 3/2010 | |
| EP | 1409670 B1 | 10/2010 | |
| EP | 1633890 B1 | 10/2010 | |
| EP | 2336317 A1 | 6/2011 | |
| EP | 2361923 A2 | 8/2011 | |
| EP | 1873259 B1 | 1/2012 | |
| EP | 2514758 A1 | 10/2012 | |
| EP | 2351852 B1 | 10/2013 | |
| EP | 2195428 B1 | 12/2013 | |
| EP | 2028278 B1 | 3/2014 | |
| EP | 2348133 B1 | 7/2014 | |
| EP | 1633770 B1 | 4/2015 | |
| EP | 2340310 B1 | 6/2015 | |
| EP | 2949752 A2 | 12/2015 | |
| EP | 2548962 B1 | 1/2016 | |
| EP | 2813582 B1 | 4/2017 | |
| WO | WO-9207065 A1 | 4/1992 | |
| WO | WO-9315187 A1 | 8/1993 | |
| WO | WO-9726270 A2 | 7/1997 | |
| WO | WO-9813526 A1 | 4/1998 | |
| WO | WO-2004044136 A2 * | 5/2004 | ........... C12N 15/113 |
| WO | WO-2009099942 A2 | 8/2009 | |
| WO | WO-2009108217 A2 | 9/2009 | |
| WO | WO-2013165816 A2 | 11/2013 | |
| WO | WO-2014154835 A2 | 10/2014 | |
| WO | WO-2015091525 A1 | 6/2015 | |
| WO | WO-2015107425 A2 | 7/2015 | |
| WO | WO-2015200223 A1 | 12/2015 | |
| WO | WO-2016028649 A1 | 2/2016 | |
| WO | WO-2017173304 A1 | 10/2017 | |

OTHER PUBLICATIONS

Shaw et al. (Nucleic Acids Research, 1991 vol. 19:747-750).*
Hawley and Gibson (Antisense Research and Development, 1992 vol. 2:119-127).*
Abramova et al. Novel oligonucleotide analogues based on morpholino nucleoside subunits-antisense technologies: new chemical possibilities. Indian Journal of Chemistry 48B:1721-1726 (2009).
Beigelman et al. Chemical modification of hammerhead ribozymes. Catalytic activity and nuclease resistance. J Biol Chem 270:25702-25708 (1995).
Burlina et al. Chemical engineering of RNase resistant and catalytically active hammerhead ribozymes. Bioorg Med Chem 5:1999-2010 (1997).
Earnshaw et al. Modified oligoribonucleotides as site-specific probes of RNA structure and function. Biopolymers (Nucleic Acid Sciences) 48:39-55 (1998).
Griffey et al. 2'-0-aminopropyl ribonucleotides: a zwitterionic modification that enhances the exonuclease resistance and biological activity of antisense oligonucleotides, J. Med. Chem. 39(26):5100-5109 (1997).
Karpeisky et al. Highly efficient synthesis of 2'-O-amino nucleosides and their incorporation in hammerhead ribozymes. Tetrahedron Lett 39:1131-1134 (1998).
Koizumi. ENA oligonucleotides as therapeutics. Curr Opin Mol Ther 8(2):144-149 (2006).
Loakes. Survey and summary: The applications of universal DNA base analogues. Nucleic Acids Research 29:2437-2447 (2001).
Martinez et al. Single-stranded antisense siRNAs guide target RNA cleavage in RNAi. Cell 110(5):563-574 (2002).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
Perrault et al. Mixed deoxyribo- and ribo-oligonucleotides with catalytic activity. Nature 344:565-568 (1990).

(56) References Cited

OTHER PUBLICATIONS

Pieken et al. Kinetic characterization of ribonuclease-resistant 2'-modified hammerhead ribozymes. Science 253:314-317 (1991).
Schwarz et al. Evidence that siRNAs function as guides, not primers, in the *Drosophila* and human RNAi pathways. Molecular Cell 10:537-548 (2002).
Singh et al. Recent developments in oligonucleotide conjugation. Chem Soc Rev 39(6):2054-2070 (2010).
Usman et al. Exploiting the chemical synthesis of RNA. Trends Biochem Sci 17:334-339 (1992).
Valtorta et al. KRAS gene amplification in colorectal cancer and impact on response to EGFR-targeted therapy. Int J Cancer 133:1259-1266 (2013).
Verma et al. Modified oligonucleotides: synthesis and strategy for users. Annu Rev Biochem 67:99-134 (1998).
Chiu et al. siRNA function in RNAi: A chemical modification analysis. RNA 9:1034-1048 (2003).
Deleavey et al. Designing chemically modified oligonucleotides for targeted gene silencing. Chem Biol. 19(8):937-954 (2012).
Jackson et al. Position-specific chemical modification of siRNAs reduces "off-target" transcript silencing. RNA 12:1197-1205 (2006).
PCT/US2017/025434 International Search Report and Written Opinion dated Jul. 10, 2017.
Behlke, M. Chemical modification of siRNAs for in vivo use. Oligonucleotides. Dec. 2008;18(4):305-319.
Corey. Chemical modification: the key to clinical application of RNA interference? J Clin Invest 117(12):3615-3622 (2007).
Levallet et al. High TUBB3 Expression, an Independent Prognostic Marker in Patients with Early Non-Small Cell Lung Cancer Treated by Preoperative Chemotherapy, Is Regulated by K-Ras Signaling Pathway. Mol Cancer Ther 11(5):1203-1213 (2012).
McCormick. KRAS as a therapeutic target. Clin Cancer Res 21(8):1797-1801 (2015).
Pecot et al. Therapeutic Silencing of KRAS Using Systemically Delivered siRNAs. Mol Cancer Ther 13(12):2876-2885 (2014).

\* cited by examiner

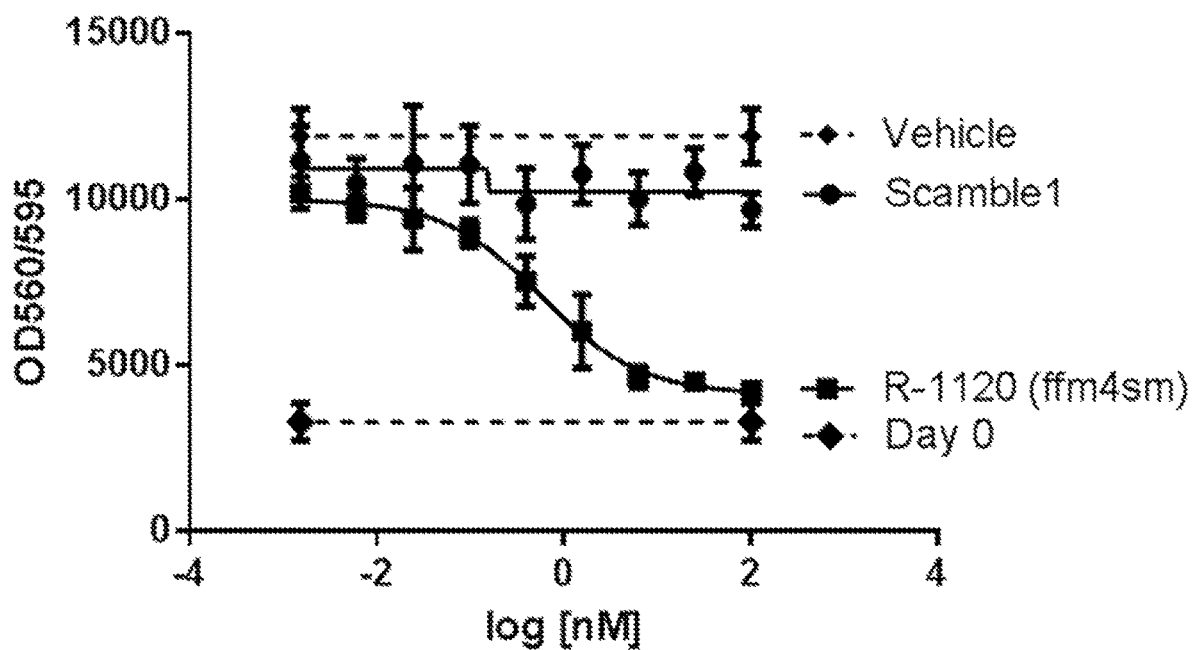

SEQUENCE LISTING

<160> NUMBER OF SEQ ID NOS: 81

<210> SEQ ID NO 1
<211> LENGTH: 23
<212> TYPE: RNA
<213> ORGANISM: Homo sapiens

<400> SEQUENCE: 1
aaaugacuga auauaaacuu gug          23

<210> SEQ ID NO 2
<211> LENGTH: 23
<212> TYPE: RNA
<213> ORGANISM: Homo sapiens

<400> SEQUENCE: 2
aaugacugaa uauaaacuug ugg          23

<210> SEQ ID NO 3
<211> LENGTH: 23
<212> TYPE: RNA
<213> ORGANISM: Homo sapiens

-continued

```
<400> SEQUENCE: 3
aacuuguggu aguuggagcu ggu                                        23

<210> SEQ ID NO 4
<211> LENGTH: 23
<212> TYPE: RNA
<213> ORGANISM: Homo sapiens

<400> SEQUENCE: 4
uaggcaagag ugccuugacg aua                                        23

<210> SEQ ID NO 5
<211> LENGTH: 23
<212> TYPE: RNA
<213> ORGANISM: Homo sapiens

<400> SEQUENCE: 5
ggcaagagug ccuugacgau aca                                        23

<210> SEQ ID NO 6
<211> LENGTH: 23
<212> TYPE: RNA
<213> ORGANISM: Homo sapiens

<400> SEQUENCE: 6
gcaagagugc cuugacgaua cag                                        23

<210> SEQ ID NO 7
<211> LENGTH: 23
<212> TYPE: RNA
<213> ORGANISM: Homo sapiens

<400> SEQUENCE: 7
caagagugcc uugacgauac agc                                        23

<210> SEQ ID NO 8
<211> LENGTH: 23
<212> TYPE: RNA
<213> ORGANISM: Homo sapiens

<400> SEQUENCE: 8
agugccuuga cgauacagcu aau                                        23

<210> SEQ ID NO 9
<211> LENGTH: 23
<212> TYPE: RNA
<213> ORGANISM: Homo sapiens

<400> SEQUENCE: 9
gugccuugac gauacagcua auu                                        23

<210> SEQ ID NO 10
<211> LENGTH: 23
<212> TYPE: RNA
<213> ORGANISM: Homo sapiens

<400> SEQUENCE: 10
ccuugacgau acagcuaauu cag                                        23

<210> SEQ ID NO 11
<211> LENGTH: 23
<212> TYPE: RNA
<213> ORGANISM: Homo sapiens
```

<400> SEQUENCE: 11
cuugacgaua cagcuaauuc aga                                              23

<210> SEQ ID NO 12
<211> LENGTH: 23
<212> TYPE: RNA
<213> ORGANISM: Homo sapiens

<400> SEQUENCE: 12
uacagcuaau ucagaaucau uuu                                              23

<210> SEQ ID NO 13
<211> LENGTH: 23
<212> TYPE: RNA
<213> ORGANISM: Homo sapiens

<400> SEQUENCE: 13
uuguggacga auaugaucca aca                                              23

<210> SEQ ID NO 14
<211> LENGTH: 23
<212> TYPE: RNA
<213> ORGANISM: Homo sapiens

<400> SEQUENCE: 14
uggacgaaua ugauccaaca aua                                              23

<210> SEQ ID NO 15
<211> LENGTH: 23
<212> TYPE: RNA
<213> ORGANISM: Homo sapiens

<400> SEQUENCE: 15
ggacgaauau gauccaacaa uag                                              23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
augacugaau auaaacuugt t                                                21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
caaguuuaua uucagucaut t                                                21

<210> SEQ ID NO 18

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 18
ugacugaaua uaaacuugut t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 19
acaaguuuau auucagucat t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 20
cuugugguag uuggagcugt t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 21
cagcuccaac uaccacaagt t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 22
ggcaagagug ccuugacgat t                                              21

```
<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
ucgucaaggc acucuugcct t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
caagagugcc uugacgauat t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
uaucgucaag gcacucuugt t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
aagagugccu ugacgauact t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
guaucgucaa ggcacucuut t                                              21
```

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 28
agagugccuu gacgauacat t                                          21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 29
uguaucguca aggcacucut t                                          21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 30
ugccuugacg auacagcuat t                                          21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 31
uagcuguauc gucaaggcat t                                          21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 32
gccuugacga uacagcuaat t                                          21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
uuagcuguau cgucaaggct t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
uugacgauac agcuaauuct t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
gaauuagcug uaucgucaat t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
ugacgauaca gcuaauucat t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
ugaauuagcu guaucgucat t                                            21

```
<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
```
cagcuaauuc agaaucauut t                                            21

```
<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
```
aaugauucug aauuagcugt t                                            21

```
<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
```
guggacgaau augauccaat t                                            21

```
<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
```
uuggaucaua uucguccact t                                            21

```
<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
```
gacgaauaug auccaacaat t                                         21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
uuguuggauc auauucguct t                                         21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
acgaauauga uccaacaaut t                                         21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
auuguuggau cauauucgut t                                         21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
augacugaau auaaacuugt t                                         21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
caaguuuaua uucagucaut t                                         21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
ugacugaaua uaaacuugut t                                         21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
acaaguuuau auucagucat t                                         21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
cuugugguag uuggagcugt t                                         21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
cagcuccaac uaccacaagt t                                         21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 52
ggcaagagug ccuugacgat t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
ucgucaaggc acucuugcct t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
caagagugcc uugacgauat t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
uaucgucaag gcacucuugt t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
aagagugccu ugacgauact t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 57
guaucgucaa ggcacucuut t                                             21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
agagugccuu gacgauacat t                                             21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
uguaucguca aggcacucut t                                             21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
ugccuugacg auacagcuat t                                             21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
uagcuguauc gucaaggcat t                                             21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 62
gccuugacga uacagcuaat t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 63
uuagcuguau cgucaaggct t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
uugacgauac agcuaauuct t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65
gaauuagcug uaucgucaat t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
ugacgauaca gcuaauucat t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 67
ugaauuagcu guaucgucat t                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
cagcuaauuc agaaucauut t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
aaugauucug aauuagcugt t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
guggacgaau augauccaat t                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
uuggaucaua uucguccact t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 72
gacgaauaug auccaacaat t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
uuguuggauc auauucguct t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
acgaauauga uccaacaaut t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
auuguuggau cauauucgut t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
ugacgauaca gcuaauucat t                                              21

<210> SEQ ID NO 77
<211> LENGTH: 21
<212> TYPE: DNA
<213> ORGANISM: Artificial Sequence
<220> FEATURE:

-continued

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
ugaauuagcu guaucgucat t                                              21

<210> SEQ ID NO 78
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic nucleotide
<220> FEATURE:
<221> NAME/KEY: modified_base
<222> LOCATION: (23)..(23)
<223> OTHER INFORMATION: Inverted abasic nucleotide

<400> SEQUENCE: 78
nugacgauac agcuaauuca uun                                            23

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
ugaauuagcu guaucgucau u                                              21

<210> SEQ ID NO 80
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic nucleotide
<220> FEATURE:
<221> NAME/KEY: modified_base
<222> LOCATION: (23)..(23)
<223> OTHER INFORMATION: Inverted abasic nucleotide

<400> SEQUENCE: 80
nugacgauac agcuaauuca uun                                            23

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
ugaauuagcu guaucgucau u                                              21

KRAS NUCLEIC ACIDS AND USES THEREOF

CROSS-REFERENCE

This application claims the benefit of U.S. Provisional Application No. 62/316,937, filed Apr. 1, 2016, which application is incorporated herein by reference.

SEQUENCE LISTING

The instant application contains a Sequence Listing which has been submitted electronically in ASCII format and is hereby incorporated by reference in its entirety. Said ASCII copy, created on Mar. 24, 2017, is named 45532-708_201_SL.txt and is 23,860 bytes in size.

BACKGROUND OF THE DISCLOSURE

Gene suppression by RNA-induced gene silencing provides several levels of control: transcription inactivation, small interfering RNA (siRNA)-induced mRNA degradation, and siRNA-induced transcriptional attenuation. In some instances, RNA interference (RNAi) provides long lasting effect over multiple cell divisions. As such, RNAi represents a viable method useful for drug target validation, gene function analysis, pathway analysis, and disease therapeutics.

SUMMARY OF THE DISCLOSURE

Disclosed herein, in certain embodiments, are molecules and pharmaceutical compositions for modulating KRAS function and/or expression in a cell.

Disclosed herein, in certain embodiments, is a polynucleic acid molecule that mediates RNA interference against KRAS, wherein the polynucleic acid molecule comprises at least one 2' modified nucleotide, at least one modified internucleotide linkage, or at least one inverted abasic moiety.

In some embodiments, the at least one 2' modified nucleotide comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified nucleotide. In some embodiments, the at least one 2' modified nucleotide comprises locked nucleic acid (LNA) or ethylene nucleic acid (ENA). In some embodiments, the at least one inverted basic moiety is at at least one terminus. In some embodiments, the at least one modified internucleotide linkage comprises a phosphorothioate linkage or a phosphorodithioate linkage.

In some embodiments, the polynucleic acid molecule is at least from about 10 to about 30 nucleotides in length. In some embodiments, the polynucleic acid molecule is at least one of: from about 15 to about 30, from about 18 to about 25, form about 18 to about 24, from about 19 to about 23, or from about 20 to about 22 nucleotides in length. In some embodiments, the polynucleic acid molecule is at least about 16, 17, 18, 19, 20, 21, 22, 23, 24, or 25 nucleotides in length.

In some embodiments, the polynucleic acid molecule comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification.

In some embodiments, the polynucleic acid molecule comprises at least one of: from about 10% to about 90% modification, from about 20% to about 90% modification, from about 30% to about 90% modification, from about 40% to about 90% modification, from about 50% to about 90% modification, from about 60% to about 90% modification, from about 70% to about 90% modification, and from about 80% to about 100% modification.

In some embodiments, the polynucleic acid molecule comprises at least one of: from about 10% to about 80% modification, from about 20% to about 80% modification, from about 30% to about 80% modification, from about 40% to about 80% modification, from about 50% to about 80% modification, from about 60% to about 80% modification, and from about 70% to about 80% modification.

In some embodiments, the polynucleic acid molecule comprises at least one of: from about 10% to about 70% modification, from about 20% to about 70% modification, from about 30% to about 70% modification, from about 40% to about 70% modification, from about 50% to about 70% modification, and from about 60% to about 70% modification.

In some embodiments, the polynucleic acid molecule comprises at least one of: from about 10% to about 60% modification, from about 20% to about 60% modification, from about 30% to about 60% modification, from about 40% to about 60% modification, and from about 50% to about 60% modification.

In some embodiments, the polynucleic acid molecule comprises at least one of: from about 10% to about 50% modification, from about 20% to about 50% modification, from about 30% to about 50% modification, and from about 40% to about 50% modification.

In some embodiments, the polynucleic acid molecule comprises at least one of: from about 10% to about 40% modification, from about 20% to about 40% modification, and from about 30% to about 40% modification.

In some embodiments, the polynucleic acid molecule comprises at least one of: from about 10% to about 30% modification, and from about 20% to about 30% modification.

In some embodiments, the polynucleic acid molecule comprises from about 10% to about 20% modification.

In some embodiments, the polynucleic acid molecule comprises from about 15% to about 90%, from about 20% to about 80%, from about 30% to about 70%, or from about 40% to about 60% modifications.

In some embodiments, the polynucleic acid molecule comprises at least about 15%, 20%, 30%, 40%, 50%, 60%, 70%, 80%, 90%, 95%, or 99% modification.

In some embodiments, the polynucleic acid molecule comprises at least about 3, about 4, about 5, about 6, about 7, about 8, about 9, about 10, about 11, about 12, about 13, about 14, about 15, about 16, about 17, about 18, about 19, about 20, about 21, about 22, or more modifications.

In some embodiments, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, or more modified nucleotides.

In some embodiments, the polynucleic acid molecule comprises a sequence that hybridizes to a target sequence selected from SEQ ID NOs: 1-15.

In some embodiments, the polynucleic acid molecule comprises a single strand.

In some embodiments, the polynucleic acid molecule comprises two or more strands.

In some embodiments, the polynucleic acid molecule comprises a first polynucleotide and a second polynucleotide hybridized to the first polynucleotide to form a double-stranded polynucleic acid molecule.

In some embodiments, the second polynucleotide comprises at least one modification.

In some embodiments, the first polynucleotide and the second polynucleotide are RNA molecules. In some embodiments, the first polynucleotide and the second polynucleotide are siRNA molecules.

In some embodiments, the first polynucleotide comprises a sequence having at least 60%, 65%, 70%, 75%, 80%, 85%, 90%, 95%, 96%, 97%, 98%, 99%, or 100% sequence identity to SEQ ID NOs: 16-81. In some embodiments, the first polynucleotide consists of a sequence selected from SEQ ID NOs: 16-81. In some embodiments, the second polynucleotide comprises a sequence having at least 60%, 65%, 70%, 75%, 80%, 85%, 90%, 95%, 96%, 97%, 98%, 99%, or 100% sequence identity to SEQ ID NOs: 16-81. In some embodiments, the second polynucleotide consists of a sequence selected from SEQ ID NOs: 16-81.

Disclosed herein, in certain embodiments, is a pharmaceutical composition comprising: a) a molecule disclosed above; and b) a pharmaceutically acceptable excipient. In some embodiments, the pharmaceutical composition is formulated as a nanoparticle formulation. In some embodiments, the pharmaceutical composition is formulated for parenteral, oral, intranasal, buccal, rectal, or transdermal administration.

Disclosed herein, in certain embodiments, is a method of treating a disease or disorder in a patient in need thereof, comprising administering to the patient a composition comprising a molecule disclosed above. In some embodiments, the disease or disorder is a cancer. In some embodiments, the cancer is a solid tumor. In some embodiments, the cancer is a hematologic malignancy. In some embodiments, the cancer comprises a KRAS-associated cancer. In some embodiments, the cancer comprises bladder cancer, breast cancer, colorectal cancer, endometrial cancer, esophageal cancer, glioblastoma multiforme, head and neck cancer, kidney cancer, lung cancer, ovarian cancer, pancreatic cancer, prostate cancer, or thyroid cancer. In some embodiments, the cancer comprises acute myeloid leukemia, CLL, DLBCL, or multiple myeloma.

Disclosed herein, in certain embodiments, is a method of inhibiting the expression of KRAS gene in a primary cell of a patient, comprising administering a molecule disclosed above to the primary cell. In some embodiments, the method is an in vivo method. In some embodiments, the patient is a human.

Disclosed herein, in certain embodiments, is a kit comprising a molecule disclosed above.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates reductions in cell viability of H358 cell in 3D culture after transfection of anti-KRAS siRNA (siRNA R-1120) with RNAiMAX.

DETAILED DESCRIPTION OF THE DISCLOSURE

Kirsten Rat Sarcoma Viral Oncogene Homolog (also known as GTPase KRas, V-Ki-ras2 Kirsten rat sarcoma viral oncogene homolog, or KRAS) is involved in regulating cell division. The K-Ras protein is a GTPase belonging to the Ras superfamily. In some instances, K-Ras modulates cell cycle progression, as well as induces growth arrest, apoptosis, and replicative senescence under different environmental triggers (e.g., cellular stress, ultraviolet, heat shock, or ionizing irradiation). In some cases, wild type KRAS gene has been shown to be frequently lost during tumor progression in different types of cancer, while mutations of KRAS gene have been linked to cancer development. In some instances, KRAS amplification has also been implicated in cancer development (see, for example, Valtorta et al. "KRAS gene amplification in colorectal cancer and impact on response to EGFR-targeted therapy," *Int. J. Cancer* 133: 1259-1266 (2013)). In such cases, the cancer pertains to a refractory cancer in which the patient has acquired resistance to a particular inhibitor or class of inhibitors.

Disclosed herein, in certain embodiments, are polynucleic acid molecules and pharmaceutical compositions that modulate the expression of KRAS. In some instances, the polynucleic acid molecules and pharmaceutical compositions modulate the expression of wild type KRAS gene. In other instances, the polynucleic acid molecules and pharmaceutical compositions modulate the expression of mutant KRAS.

In some embodiments, the polynucleic acid molecules and pharmaceutical compositions are used for the treatment of a disease or disorder (e.g., cancer or a KRAS-associated disease or disorder). In additional embodiments, the polynucleic acid molecules and pharmaceutical compositions are used for inhibiting the expression of KRAS gene in a primary cell of a patient in need thereof.

In additional cases, also included herein are kits that comprise one or more of polynucleic acid molecules and pharmaceutical compositions described herein.

Polynucleic Acid Molecule

In some embodiments, a polynucleic acid molecule described herein modulates the expression of the KRAS gene (GenBank: BC010502.1). In some embodiments, the KRAS gene is wild type or comprises a mutation. In some instances, KRAS mRNA is wild type or comprises a mutation. In some instances, the polynucleic acid molecule is a polynucleic acid molecule that hybridizes to a target region of wild type KRAS DNA or RNA. In some instances, the polynucleic acid molecule is a polynucleic acid molecule that hybridizes to a target region of KRAS DNA or RNA comprising a mutation (e.g., a substitution, a deletion, or an addition).

In some embodiments, KRAS DNA or RNA comprises one or more mutations. In some embodiments, KRAS DNA or RNA comprises one or more mutations at codons 12 or 13 in exon 1. In some instances, KRAS DNA or RNA comprises one or more mutations at codons 61, 63, 117, 119, or 146. In some instances, KRAS DNA or RNA comprises one or more mutations at positions corresponding to amino acid residues 12, 13, 18, 19, 20, 22, 24, 26, 36, 59, 61, 63, 64, 68, 110, 116, 117, 119, 146, 147, 158, 164, 176, or a combination thereof of the KRAS polypeptide. In some embodiments, KRAS DNA or RNA comprises one or more mutations at positions corresponding to amino acid residues selected from G12V, G12D, G12C, G12A, G12S, G12F, G13C, G13D, G13V, A18D, L19F, T20R, Q22K, I24N, N26K, I36L, I36M, A59G, A59E, Q61K, Q61H, Q61L, Q61R, E63K, Y64D, Y64N, R68S, P110S, K117N, C118S, A146T, A146P, A146V, K147N, T158A, R164Q, K176Q, or a combination thereof of the KRAS polypeptide.

In some embodiments, a polynucleic acid molecule hybridizes to a target region of KRAS DNA or RNA comprising one or more mutations. In some embodiments, the polynucleic acid molecule hybridizes to a target region of KRAS DNA or RNA comprising one or more mutations at codons 12 or 13 in exon 1. In some embodiments, the polynucleic acid molecule hybridizes to a target region of KRAS DNA or RNA comprising one or more mutations at codons 61, 63, 117, 119, or 146. In some embodiments, the polynucleic acid molecule hybridizes to a target region of KRAS DNA or RNA comprising one or more mutations at positions corresponding to amino acid residues 12, 13, 18, 19, 20, 22, 24, 26, 36, 59, 61, 63, 64, 68, 110, 116, 117, 119, 146, 147, 158, 164, 176, or a combination thereof of the KRAS polypeptide. In some embodiments, the polynucleic acid molecule hybridizes to a target region of KRAS DNA or RNA comprising one or more mutations corresponding to amino acid residues selected from G12V, G12D, G12C, G12A, G12S, G12F, G13C, G13D, G13V, A18D, L19F, T20R, Q22K, I24N, N26K, I36L, I36M, A59G, A59E, Q61K, Q61H, Q61L, Q61R, E63K, Y64D, Y64N, R68S, P110S, K117N, C118S, A146T, A146P, A146V, K147N, T158A, R164Q, K176Q, or a combination thereof of the KRAS polypeptide.

In some embodiments, a polynucleic acid molecule comprises a sequence that hybridizes to a target sequence illustrated in Table 1. In some embodiments, the polynucleic acid molecule hybridizes to a KRAS target sequence selected from SEQ ID NOs: 1-15. In some cases, the polynucleic acid molecule hybridizes to a KRAS target sequence selected from SEQ ID NOs: 1-15 with less than 5 mismatched bases, with less than 4 mismatched bases, with less than 3 mismatched bases, with less than 2 mismatched bases, or with 1 mismatched base. In some cases, the polynucleic acid molecule hybridizes to a KRAS target sequence selected from SEQ ID NOs: 1-15 with less than 4 mismatched bases.

In some embodiments, a polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence listed in Table 2, Table 3, or Table 6. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to SEQ ID NOs: 16-81. In some embodiments, the polynucleic acid molecule comprises a sequence having at least 50% sequence identity to SEQ ID NOs: 16-81. In some embodiments, the polynucleic acid molecule comprises a sequence having at least 60% sequence identity to SEQ ID NOs: 16-81. In some embodiments, the polynucleic acid molecule comprises a sequence having at least 70% sequence identity to SEQ ID NOs: 16-81. In some embodiments, the polynucleic acid molecule comprises a sequence having at least 75% sequence identity to SEQ ID NOs: 16-81. In some embodiments, the polynucleic acid molecule comprises a sequence having at least 80% sequence identity to SEQ ID NOs: 16-81. In some embodiments, the polynucleic acid molecule comprises a sequence having at least 85% sequence identity to SEQ ID NOs: 16-81. In some embodiments, the polynucleic acid molecule comprises a sequence having at least 90% sequence identity to SEQ ID NOs: 16-81. In some embodiments, the polynucleic acid molecule comprises a sequence having at least 95% sequence identity to SEQ ID NOs: 16-81. In some embodiments, the polynucleic acid molecule comprises a sequence having at least 96% sequence identity to SEQ ID NOs: 16-81. In some embodiments, the polynucleic acid molecule comprises a sequence having at least 97% sequence identity to SEQ ID NOs: 16-81. In some embodiments, the polynucleic acid molecule comprises a sequence having at least 98% sequence identity to SEQ ID NOs: 16-81. In some embodiments, the polynucleic acid molecule comprises a sequence having at least 99% sequence identity to SEQ ID NOs: 16-81. In some embodiments, the polynucleic acid molecule consists of SEQ ID NOs: 16-81.

In some embodiments, a polynucleic acid molecule comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to SEQ ID NOs: 16-81. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to SEQ ID NOs: 16-81. In some cases, the polynucleic acid molecule comprises a first polynucleotide having at least 50%, 55%, 60%, 65%, 70%, 75%, 80%, 85%, 90%, 95%, 96%, 97%, 98%, 99%, or 100% sequence identity to SEQ ID NOs: 16-81 and a second polynucleotide having at least 50%, 55%, 60%, 65%, 70%, 75%, 80%, 85%, 90%, 95%, 96%, 97%, 98%, 99%, or 100% sequence identity to SEQ ID NOs: 16-81.

In some embodiments, a polynucleic acid molecule described herein comprises RNA or DNA. In some cases, the polynucleic acid molecule comprises RNA. In some instances, RNA comprises short interfering RNA (siRNA), short hairpin RNA (shRNA), microRNA (miRNA), double-stranded RNA (dsRNA), transfer RNA (tRNA), ribosomal RNA (rRNA), or heterogeneous nuclear RNA (hnRNA). In some instances, RNA comprises shRNA. In some instances, RNA comprises miRNA. In some instances, RNA comprises dsRNA. In some instances, RNA comprises tRNA. In some instances, RNA comprises rRNA. In some instances, RNA comprises hnRNA. In some instances, the RNA comprises siRNA. In some instances, the polynucleic acid molecule comprises siRNA.

In some embodiments, a polynucleic acid molecule is from about 10 to about 50 nucleotides in length. In some instances, the polynucleic acid molecule is from about 10 to about 30, from about 15 to about 30, from about 18 to about 25, from about 18 to about 24, from about 19 to about 23, or from about 20 to about 22 nucleotides in length.

In some embodiments, a polynucleic acid molecule is about 50 nucleotides in length. In some instances, the polynucleic acid molecule is about 45 nucleotides in length. In some instances, the polynucleic acid molecule is about 40 nucleotides in length. In some instances, the polynucleic acid molecule is about 35 nucleotides in length. In some instances, the polynucleic acid molecule is about 30 nucleotides in length. In some instances, the polynucleic acid molecule is about 25 nucleotides in length. In some instances, the polynucleic acid molecule is about 20 nucleotides in length. In some instances, the polynucleic acid molecule is about 19 nucleotides in length. In some instances, the polynucleic acid molecule is about 18 nucleotides in length. In some instances, the polynucleic acid molecule is about 17 nucleotides in length. In some instances, the polynucleic acid molecule is about 16 nucleotides in length. In some instances, the polynucleic acid molecule is about 15 nucleotides in length. In some instances, the polynucleic acid molecule is about 14 nucleotides in length. In some instances, the polynucleic acid molecule is about 13 nucleotides in length. In some instances, the polynucleic acid molecule is about 12 nucleotides in length. In some instances, the polynucleic acid molecule is about 11 nucleotides in length. In some instances, the polynucleic acid molecule is about 10 nucleotides in length. In some instances, the polynucleic acid molecule is from about 10 to about 50 nucleotides in length. In some instances, the polynucleic acid molecule is from about 10 to about 45 nucleotides in length. In some instances, the polynucleic acid molecule is from about 10 to about 40 nucleotides in length. In some instances, the polynucleic acid molecule is from about 10 to about 35 nucleotides in length. In some instances, the polynucleic acid molecule is from about 10 to about 30 nucleotides in length. In some instances, the polynucleic acid molecule is from about 10 to about 25 nucleotides in length. In some instances, the polynucleic acid molecule is from about 10 to about 20 nucleotides in length. In some instances, the polynucleic acid molecule is from about 15 to about 25 nucleotides in length. In some instances, the polynucleic acid molecule is from about 15 to about 30 nucleotides in length. In some instances, the polynucleic acid molecule is from about 12 to about 30 nucleotides in length.

In some embodiments, a polynucleic acid molecule comprises a first polynucleotide. In some instances, the polynucleic acid molecule comprises a second polynucleotide. In some instances, the polynucleic acid molecule comprises a first polynucleotide and a second polynucleotide. In some instances, the first polynucleotide is a sense strand or passenger strand. In some instances, the second polynucleotide is an antisense strand or guide strand.

In some embodiments, a polynucleic acid molecule described herein is a first polynucleotide. In some embodiments, the first polynucleotide is from about 10 to about 50 nucleotides in length. In some instances, the first polynucleotide is from about 10 to about 30, from about 15 to about 30, from about 18 to about 25, from about 18 to about 24, from about 19 to about 23, or from about 20 to about 22 nucleotides in length.

In some instances, a first polynucleotide is about 50 nucleotides in length. In some instances, the first polynucleotide is about 45 nucleotides in length. In some instances, the first polynucleotide is about 40 nucleotides in length. In some instances, the first polynucleotide is about 35 nucleotides in length. In some instances, the first polynucleotide is about 30 nucleotides in length. In some instances, the first polynucleotide is about 25 nucleotides in length. In some instances, the first polynucleotide is about 20 nucleotides in length. In some instances, the first polynucleotide is about 19 nucleotides in length. In some instances, the first polynucleotide is about 18 nucleotides in length. In some instances, the first polynucleotide is about 17 nucleotides in length. In some instances, the first polynucleotide is about 16 nucleotides in length. In some instances, the first polynucleotide is about 15 nucleotides in length. In some instances, the first polynucleotide is about 14 nucleotides in length. In some instances, the first polynucleotide is about 13 nucleotides in length. In some instances, the first polynucleotide is about 12 nucleotides in length. In some instances, the first polynucleotide is about 11 nucleotides in length. In some instances, the first polynucleotide is about 10 nucleotides in length. In some instances, the first polynucleotide is from about 10 to about 50 nucleotides in length. In some instances, the first polynucleotide is from about 10 to about 45 nucleotides in length. In some instances, the first polynucleotide is from about 10 to about 40 nucleotides in length. In some instances, the first polynucleotide is from about 10 to about 35 nucleotides in length. In some instances, the first polynucleotide is from about 10 to about 30 nucleotides in length. In some instances, the first polynucleotide is from about 10 to about 25 nucleotides in length. In some instances, the first polynucleotide is from about 10 to about 20 nucleotides in length. In some instances, the first polynucleotide is from about 15 to about 25 nucleotides in length. In some instances, the first polynucleotide is from about 15 to about 30 nucleotides in length. In some instances, the first polynucleotide is from about 12 to about 30 nucleotides in length.

In some embodiments, a polynucleic acid molecule described herein is a second polynucleotide. In some embodiments, the second polynucleotide is from about 10 to about 50 nucleotides in length. In some instances, the second polynucleotide is from about 10 to about 30, from about 15 to about 30, from about 18 to about 25, from about 18 to about 24, from about 19 to about 23, or from about 20 to about 22 nucleotides in length.

In some instances, a second polynucleotide is about 50 nucleotides in length. In some instances, the second polynucleotide is about 45 nucleotides in length. In some instances, the second polynucleotide is about 40 nucleotides in length. In some instances, the second polynucleotide is about 35 nucleotides in length. In some instances, the second polynucleotide is about 30 nucleotides in length. In some instances, the second polynucleotide is about 25 nucleotides in length. In some instances, the second polynucleotide is about 20 nucleotides in length. In some instances, the second polynucleotide is about 19 nucleotides in length. In some instances, the second polynucleotide is about 18 nucleotides in length. In some instances, the second polynucleotide is about 17 nucleotides in length. In some instances, the second polynucleotide is about 16 nucleotides in length. In some instances, the second polynucleotide is about 15 nucleotides in length. In some instances, the second polynucleotide is about 14 nucleotides in length. In some instances, the second polynucleotide is about 13 nucleotides in length. In some instances, the second polynucleotide is about 12 nucleotides in length. In some instances, the second polynucleotide is about 11 nucleotides in length. In some instances, the second polynucleotide is about 10 nucleotides in length. In some instances, the second polynucleotide is from about 10 to about 50 nucleotides in length. In some instances, the second polynucleotide is from about 10 to about 45 nucleotides in length. In some instances, the second polynucleotide is from about 10 to about 40 nucleotides in length. In some instances, the second polynucleotide is from about 10 to about 35 nucleotides in length. In some instances, the second polynucleotide is from about 10 to about 30 nucleotides in length. In some instances, the second polynucleotide is from about 10 to about 25 nucleotides in length. In some instances, the second polynucleotide is from about 10 to about 20 nucleotides in length. In some instances, the second polynucleotide is from about 15 to about 25 nucleotides in length. In some instances, the second polynucleotide is from about 15 to about 30 nucleotides in length. In some instances, the second polynucleotide is from about 12 to about 30 nucleotides in length.

In some embodiments, a polynucleic acid molecule comprises a first polynucleotide and a second polynucleotide. In some instances, the polynucleic acid molecule further comprises a blunt terminus, an overhang, or a combination thereof. In some instances, the blunt terminus is a 5' blunt terminus, a 3' blunt terminus, or both. In some cases, the overhang is a 5' overhang, 3' overhang, or both. In some cases, the overhang comprises 1, 2, 3, 4, 5, 6, 7, 8, 9, or 10 non-base pairing nucleotides. In some cases, the overhang comprises 1, 2, 3, 4, 5, or 6 non-base pairing nucleotides. In some cases, the overhang comprises 1, 2, 3, or 4 non-base pairing nucleotides. In some cases, the overhang comprises 1 non-base pairing nucleotide. In some cases, the overhang comprises 2 non-base pairing nucleotides. In some cases, the overhang comprises 3 non-base pairing nucleotides. In some cases, the overhang comprises 4 non-base pairing nucleotides.

In some embodiments, the sequence of a polynucleic acid molecule is at least 40%, 50%, 55%, 60%, 65%, 70%, 75%, 80%, 85%, 90%, 95%, 98%, 99%, or 99.5% complementary to a target sequence described herein. In some embodiments, the sequence of the polynucleic acid molecule is at least 50% complementary to a target sequence described herein. In some embodiments, the sequence of the polynucleic acid molecule is at least 60% complementary to a target sequence described herein. In some embodiments, the sequence of the polynucleic acid molecule is at least 70% complementary to a target sequence described herein. In some embodiments, the sequence of the polynucleic acid molecule is at least 80% complementary to a target sequence described herein. In some embodiments, the sequence of the polynucleic acid molecule is at least 90% complementary to a target sequence described herein. In some embodiments, the sequence of the polynucleic acid molecule is at least 95% complementary to a target sequence described herein. In some embodiments, the sequence of the polynucleic acid molecule is at least 99% complementary to a target sequence described herein. In some instances, the sequence of the polynucleic acid molecule is 100% complementary to a target sequence described herein.

In some embodiments, the sequence of a polynucleic acid molecule has 5 or less mismatches to a target sequence described herein. In some embodiments, the sequence of the polynucleic acid molecule has 4 or less mismatches to a target sequence described herein. In some instances, the sequence of the polynucleic acid molecule has 3 or less mismatches to a target sequence described herein. In some cases, the sequence of the polynucleic acid molecule has 2 or less mismatches to a target sequence described herein. In some cases, the sequence of the polynucleic acid molecule has 1 or less mismatches to a target sequence described herein.

In some embodiments, the specificity of a polynucleic acid molecule that hybridizes to a target sequence described herein is a 95%, 98%, 99%, 99.5% or 100% sequence complementarity of the polynucleic acid molecule to a target sequence. In some instances, the hybridization is a high stringent hybridization condition.

In some embodiments, the polynucleic acid molecule hybridizes to at least 8, 9, 10, 11, 12, 13, 14, 15, 16, 17, 18, 19, 20, or more contiguous bases of a target sequence described herein. In some embodiments, the polynucleic acid molecule hybridizes to at least 8 contiguous bases of a target sequence described herein. In some embodiments, the polynucleic acid molecule hybridizes to at least 9 contiguous bases of a target sequence described herein. In some embodiments, the polynucleic acid molecule hybridizes to at least 10 contiguous bases of a target sequence described herein. In some embodiments, the polynucleic acid molecule hybridizes to at least 11 contiguous bases of a target sequence described herein. In some embodiments, the polynucleic acid molecule hybridizes to at least 12 contiguous bases of a target sequence described herein. In some embodiments, the polynucleic acid molecule hybridizes to at least 15 contiguous bases of a target sequence described herein. In some embodiments, the polynucleic acid molecule hybridizes to at least 18 contiguous bases of a target sequence described herein.

In some embodiments, a polynucleic acid molecule described herein has reduced off-target effect. In some instances, "off-target" or "off-target effects" refer to any instance in which a polynucleic acid polymer directed against a given target causes an unintended effect by interacting either directly or indirectly with another mRNA sequence, a DNA sequence, or a cellular protein or other moiety. In some instances, an "off-target effect" occurs when there is a simultaneous degradation of other transcripts due to partial homology or complementarity between that other transcript and the sense and/or antisense strand of the polynucleic acid molecule.

In some embodiments, a polynucleic acid molecule comprises natural, synthetic, or artificial nucleotide analogues or bases. In some cases, the polynucleic acid molecule comprises combinations of DNA, RNA, and/or nucleotide analogues. In some instances, the synthetic or artificial nucleotide analogues or bases comprise modifications at one or more of ribose moiety, phosphate moiety, nucleoside moiety, or a combination thereof.

In some embodiments, nucleotide analogues or artificial nucleotide base comprise a nucleic acid with a modification at a 2' hydroxyl group of the ribose moiety. In some instances, the modification includes an H, OR, R, halo, SH, SR, NH2, NHR, NR2, or CN, wherein R is an alkyl moiety. Exemplary alkyl moiety includes, but is not limited to, halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, or disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'O-methoxyethyl modification adds a methoxyethyl group to the 2' hydroxyl group of the ribose moiety. Exemplary chemical structures of a 2'-O-methyl modification of an adenosine molecule and 2'O-methoxyethyl modification of a uridine are illustrated below.

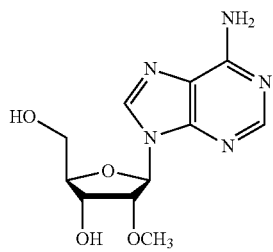

2'-O-methyl-adenosine

2'-O-methoxyethyl uridine

In some instances, the modification at the 2' hydroxyl group is a 2'-O-aminopropyl modification in which an extended amine group comprising a propyl linker binds the amine group to the 2' oxygen. In some instances, this modification neutralizes the phosphate-derived overall negative charge of the oligonucleotide molecule by introducing one positive charge from the amine group per sugar and thereby improves cellular uptake properties due to its zwitterionic properties. An exemplary chemical structure of a 2'-O-aminopropyl nucleoside phosphoramidite is illustrated below.

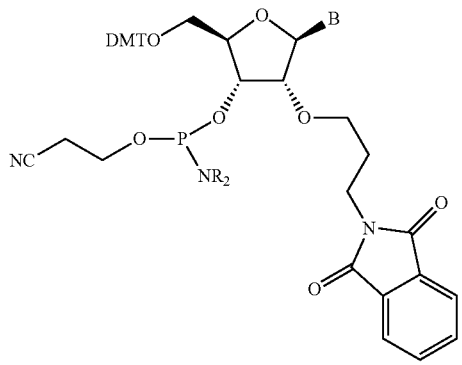

2'-O-aminopropyl nucleoside phosphoramidite

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo ($^{3}$E) conformation of the furanose ring of an LNA monomer.

LNA (Locked Nucleic Acids)

In some instances, the modification at the 2' hydroxyl group comprises ethylene nucleic acids (ENA) such as for example 2'-4'-ethylene-bridged nucleic acid, which locks the sugar conformation into a $C_3$'-endo sugar puckering conformation. ENA are part of the bridged nucleic acids class of modified nucleic acids that also comprises LNA. Exemplary chemical structures of the ENA and bridged nucleic acids are illustrated below.

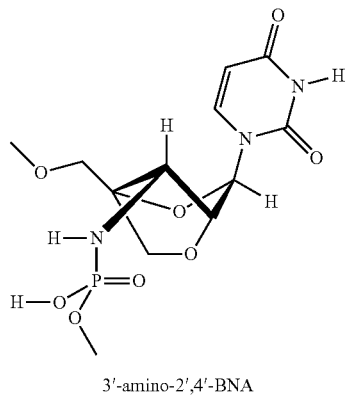

3'-amino-2',4'-BNA

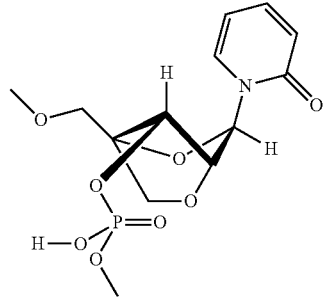

2',4'-BNA-2-pyridone

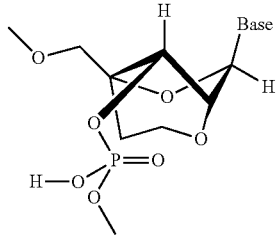

2',4'-ENA

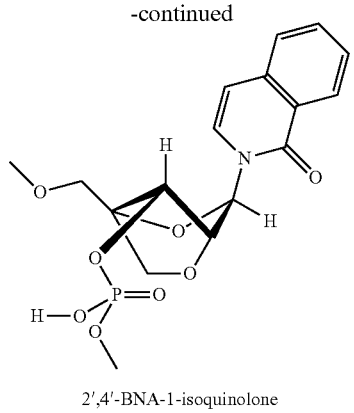

2',4'-BNA-1-isoquinolone

In some embodiments, additional modifications at the 2' hydroxyl group include 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA).

In some embodiments, nucleotide analogues comprise modified bases such as, but not limited to, 5-propynyluridine, 5-propynylcytidine, 6-methyladenine, 6-methylguanine, N, N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2, 2-dimethylguanosine, 5-methylaminoethyluridine, 5-methyloxyuridine, deazanucleotides (such as 7-deaza-adenosine, 6-azouridine, 6-azocytidine, or 6-azothymidine), 5-methyl-2-thiouridine, other thio bases (such as 2-thiouridine, 4-thiouridine, and 2-thiocytidine), dihydrouridine, pseudouridine, queuosine, archaeosine, naphthyl and substituted naphthyl groups, any O-and N-alkylated purines and pyrimidines (such as N6-methyladenosine, 5-methylcarbonylmethyluridine, uridine 5-oxyacetic acid, pyridine-4-one, or pyridine-2-one), phenyl and modified phenyl groups (such as aminophenol or 2,4, 6-trimethoxy benzene), modified cytosines that act as G-clamp nucleotides, 8-substituted adenines and guanines, 5-substituted uracils and thymines, azapyrimidines, carboxyhydroxyalkyl nucleotides, carboxyalkylaminoalkyi nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are, or are based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include, but are not limited to, 3-nitropyrrole, 5-nitroindole, or nebularine.

In some embodiments, nucleotide analogues further comprise morpholinos, peptide nucleic acids (PNAs), methylphosphonate nucleotides, thiolphosphonate nucleotides, 2'-fluoro N3-P5'-phosphoramidites, 1', 5'-anhydrohexitol nucleic acids (HNAs), or a combination thereof. Morpholino or phosphorodiamidate morpholino oligo (PMO) comprises synthetic molecules whose structure mimics natural nucleic acid structure but deviates from the normal sugar and phosphate structures. In some instances, the five member ribose ring is substituted with a six member morpholino ring containing four carbons, one nitrogen, and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides.

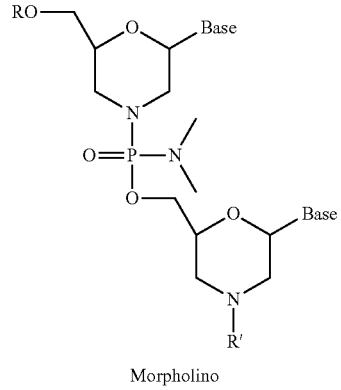

Morpholino

In some embodiments, peptide nucleic acid (PNA) does not contain sugar ring or phosphate linkage and the bases are attached and appropriately spaced by oligoglycine-like molecules, therefore eliminating a backbone charge.

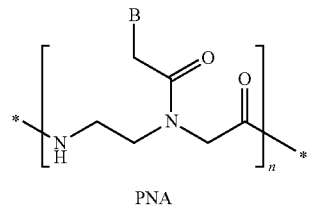

PNA

In some embodiments, one or more modifications optionally occur at the internucleotide linkage. In some instances, modified internucleotide linkage includes, but is not limited to, phosphorothioates; phosphorodithioates; methylphosphonates; 5'-alkylenepho sphonates; 5'-methylphosphonate; 3'-alkylene phosphonates; borontrifluoridates; borano phosphate esters and selenophosphates of 3'-5'linkage or 2'-5'linkage; phosphotriesters; thionoalkylphosphotriesters; hydrogen phosphonate linkages; alkyl phosphonates; alkylphosphonothioates; arylphosphonothioates; phosphoroselenoates; phosphorodiselenoates; phosphinates; phosphoramidates; 3'-alkylphosphoramidates; aminoalkylphosphoramidates; thionophosphoramidates; phosphoropiperazidates; phosphoroanilothioates; phosphoroanilidates; ketones; sulfones; sulfonamides; carbonates; carbamates; methylenehydrazos; methylenedimethylhydrazos; formacetals; thioformacetals; oximes; methyleneiminos; methylenemethyliminos; thioamidates; linkages with riboacetyl groups; aminoethyl glycine; silyl or siloxane linkages; alkyl or cycloalkyl linkages with or without heteroatoms of, for example, 1 to 10 carbons that are saturated or unsaturated and/or substituted and/or contain heteroatoms; linkages with morpholino structures, amides, or polyamides wherein the bases are attached to the aza nitrogens of the backbone directly or indirectly; and combinations thereof.

In some instances, the modification is a methyl or thiol modification such as methylphosphonate or thiolphosphonate modification. Exemplary thiolphosphonate nucleotide (left) and methylphosphonate nucleotide (right) are illustrated below.

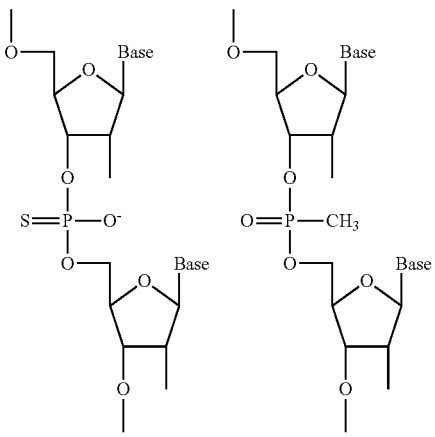

In some instances, a modified nucleotide includes, but is not limited to, 2'-fluoro N3-P5'-phosphoramidites illustrated as:

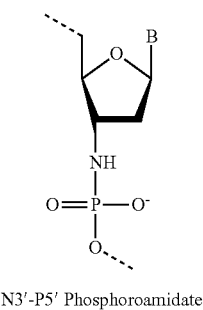

N3'-P5' Phosphoroamidate

In some instances, a modified nucleotide includes, but is not limited to, hexitol nucleic acid (or 1', 5'-anhydrohexitol nucleic acids (HNA)) illustrated as:

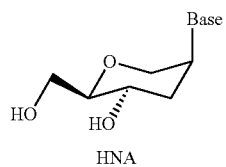

HNA

In some embodiments, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3'-terminus is optionally conjugated with an aminoalkyl group, e.g., a 3' C5-aminoalkyl dT. In an additional alternative, the 3'-terminus is optionally conjugated with an abasic site, e.g., with an apurinic or apyrimidinic site. In some instances, the 5'-terminus is conjugated with an aminoalkyl group, e.g., a 5'-O-alkylamino substituent. In some cases, the 5'-terminus is conjugated with an abasic site, e.g., with an apurinic or apyrimidinic site.

In some embodiments, the polynucleic acid molecule comprises one or more of the artificial nucleotide analogues described herein. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methyl modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of thiolphosphonate nucleotides.

In some instances, a polynucleic acid molecule comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification. In some instances, the polynucleic acid molecule is a polynucleic acid molecule of SEQ ID NOs: 16-81.

In some cases, a polynucleic acid molecule comprises at least one of: from about 10% to about 90% modification, from about 20% to about 90% modification, from about 30% to about 90% modification, from about 40% to about 90% modification, from about 50% to about 90% modification, from about 60% to about 90% modification, from about 70% to about 90% modification, and from about 80% to about 100% modification. In some instances, the polynucleic acid molecule is a polynucleic acid molecule of SEQ ID NOs: 16-81.

In some cases, a polynucleic acid molecule comprises at least one of: from about 10% to about 80% modification, from about 20% to about 80% modification, from about 30% to about 80% modification, from about 40% to about 80% modification, from about 50% to about 80% modification, from about 60% to about 80% modification, and from about 70% to about 80% modification. In some instances, the polynucleic acid molecule is a polynucleic acid molecule of SEQ ID NOs: 16-81.

In some instances, a polynucleic acid molecule comprises at least one of: from about 10% to about 70% modification, from about 20% to about 70% modification, from about 30% to about 70% modification, from about 40% to about 70% modification, from about 50% to about 70% modification, and from about 60% to about 70% modification. In some instances, the polynucleic acid molecule is a polynucleic acid molecule of SEQ ID NOs: 16-81.

In some instances, a polynucleic acid molecule comprises at least one of: from about 10% to about 60% modification, from about 20% to about 60% modification, from about 30% to about 60% modification, from about 40% to about 60% modification, and from about 50% to about 60% modification. In some instances, the polynucleic acid molecule is a polynucleic acid molecule of SEQ ID NOs: 16-81.

In some cases, a polynucleic acid molecule comprises at least one of: from about 10% to about 50% modification, from about 20% to about 50% modification, from about 30% to about 50% modification, and from about 40% to about 50% modification. In some instances, the polynucleic acid molecule is a polynucleic acid molecule of SEQ ID NOs: 16-81.

In some cases, a polynucleic acid molecule comprises at least one of: from about 10% to about 40% modification, from about 20% to about 40% modification, and from about 30% to about 40% modification. In some instances, the polynucleic acid molecule is a polynucleic acid molecule of SEQ ID NOs: 16-81.

In some cases, a polynucleic acid molecule comprises at least one of: from about 10% to about 30% modification, and from about 20% to about 30% modification. In some instances, the polynucleic acid molecule is a polynucleic acid molecule of SEQ ID NOs: 16-81.

In some cases, a polynucleic acid molecule comprises from about 10% to about 20% modification. In some instances, the polynucleic acid molecule is a polynucleic acid molecule of SEQ ID NOs: 16-81.

In some cases, a polynucleic acid molecule comprises from about 15% to about 90%, from about 20% to about 80%, from about 30% to about 70%, or from about 40% to about 60% modifications. In some instances, the polynucleic acid molecule is a polynucleic acid molecule of SEQ ID NOs: 16-81.

In additional cases, a polynucleic acid molecule comprises at least about 15%, 20%, 30%, 40%, 50%, 60%, 70%, 80%, 90%, 95%, or 99% modification. In some instances, the polynucleic acid molecule is a polynucleic acid molecule of SEQ ID NOs: 16-81.

In some embodiments, a polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, or more modifications. In some instances, the polynucleic acid molecule is a polynucleic acid molecule of SEQ ID NOs: 16-81.

In some instances, a polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, or more modified nucleotides. In some instances, the polynucleic acid molecule is a polynucleic acid molecule of SEQ ID NOs: 16-81.

In some instances, from about 5 to about 100% of a polynucleic acid molecule comprise an artificial nucleotide analogue described herein. In some instances, about 5%, 10%, 15%, 20%, 25%, 30%, 35%, 40%, 45%, 50%, 55%, 60%, 65%, 70%, 75%, 80%, 85%, 90%, 95%, or 100% of a polynucleic acid molecule comprise an artificial nucleotide analogue described herein. In some instances, about 5%, 10%, 15%, 20%, 25%, 30%, 35%, 40%, 45%, 50%, 55%, 60%, 65%, 70%, 75%, 80%, 85%, 90%, 95%, or 100% of a polynucleic acid molecule of SEQ ID NOs: 16-81 comprise an artificial nucleotide analogue described herein. In some instances, about 5%, 10%, 15%, 20%, 25%, 30%, 35%, 40%, 45%, 50%, 55%, 60%, 65%, 70%, 75%, 80%, 85%, 90%, 95%, or 100% of a polynucleic acid molecule of SEQ ID NOs: 16-45 comprise an artificial nucleotide analogue described herein. In some instances, about 5% of a polynucleic acid molecule of SEQ ID NOs: 16-45 comprise an artificial nucleotide analogue described herein. In some instances, about 10% of a polynucleic acid molecule of SEQ ID NOs: 16-45 comprise an artificial nucleotide analogue described herein. In some instances, about 15% of a polynucleic acid molecule of SEQ ID NOs: 16-45 comprise an artificial nucleotide analogue described herein. In some instances, about 20% of a polynucleic acid molecule of SEQ ID NOs: 16-45 comprise an artificial nucleotide analogue described herein. In some instances, about 25% of a polynucleic acid molecule of SEQ ID NOs: 16-45 comprise an artificial nucleotide analogue described herein. In some instances, about 30% of a polynucleic acid molecule of SEQ ID NOs: 16-45 comprise an artificial nucleotide analogue described herein. In some instances, about 35% of a polynucleic acid molecule of SEQ ID NOs: 16-45 comprise an artificial nucleotide analogue described herein. In some instances, about 40% of a polynucleic acid molecule of SEQ ID NOs: 16-45 comprise an artificial nucleotide analogue described herein. In some instances, about 45% of a polynucleic acid molecule of SEQ ID NOs: 16-45 comprise an artificial nucleotide analogue described herein. In some instances, about 50% of a polynucleic acid molecule of SEQ ID NOs: 16-45 comprise an artificial nucleotide analogue described herein. In some instances, about 55% of a polynucleic acid molecule of SEQ ID NOs: 16-45 comprise an artificial nucleotide analogue described herein. In some instances, about 60% of a polynucleic acid molecule of SEQ ID NOs: 16-45 comprise an artificial nucleotide analogue described herein. In some instances, about 65% of a polynucleic acid molecule of SEQ ID NOs: 16-45 comprise an artificial nucleotide analogue described herein. In some instances, about 70% of a polynucleic acid molecule of SEQ ID NOs: 16-45 comprise an artificial nucleotide analogue described herein. In some instances, about 75% of a polynucleic acid molecule of SEQ ID NOs: 16-45 comprise an artificial nucleotide analogue described herein. In some instances, about 80% of a polynucleic acid molecule of SEQ ID NOs: 16-45 comprise an artificial nucleotide analogue described herein. In some instances, about 85% of a polynucleic acid molecule of SEQ ID NOs: 16-45 comprise an artificial nucleotide analogue described herein. In some instances, about 90% of a polynucleic acid molecule of SEQ ID NOs: 16-45 comprise an artificial nucleotide analogue described herein. In some instances, about 95% of a polynucleic acid molecule of SEQ ID NOs: 16-45 comprise an artificial nucleotide analogue described herein. In some instances, about 96% of a polynucleic acid molecule of SEQ ID NOs: 16-45 comprise an artificial nucleotide analogue described herein. In some instances, about 97% of a polynucleic acid molecule of SEQ ID NOs: 16-45 comprise an artificial nucleotide analogue described herein. In some instances, about 98% of a polynucleic acid molecule of SEQ ID NOs: 16-45 comprise an artificial nucleotide analogue described herein. In some instances, about 99% of a polynucleic acid molecule of SEQ ID NOs: 16-45 comprise an artificial nucleotide analogue described herein. In some instances, about 100% of a polynucleic acid molecule of SEQ ID NOs: 16-45 comprise an artificial nucleotide analogue described herein. In some embodiments, the artificial nucleotide analogue comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof.

In some embodiments, a polynucleic acid molecule comprises from about 1 to about 25 modifications in which the modification comprises an artificial nucleotide analogue described herein. In some embodiments, a polynucleic acid molecule of SEQ ID NOs: 16-81 comprises from about 1 to about 25 modifications in which the modifications comprise an artificial nucleotide analogue described herein. In some embodiments, a polynucleic acid molecule of SEQ ID NOs: 16-81 comprises about 1 modification in which the modification comprises an artificial nucleotide analogue described herein. In some embodiments, a polynucleic acid molecule of SEQ ID NOs: 16-81 comprises about 2 modifications in which the modifications comprise an artificial nucleotide analogue described herein. In some embodiments, a polynucleic acid molecule of SEQ ID NOs: 16-81 comprises about 3 modifications in which the modifications comprise an artificial nucleotide analogue described herein. In some embodiments, a polynucleic acid molecule of SEQ ID NOs: 16-81 comprises about 4 modifications in which the modifications comprise an artificial nucleotide analogue described herein. In some embodiments, a polynucleic acid molecule of SEQ ID NOs: 16-81 comprises about 5 modifications in which the modifications comprise an artificial nucleotide analogue described herein. In some embodiments, a polynucleic acid molecule of SEQ ID NOs: 16-81 comprises about 6 modifications in which the modifications comprise an artificial nucleotide analogue described herein. In some embodiments, a polynucleic acid molecule of SEQ ID NOs: 16-81 comprises about 7 modifications in which the modifications comprise an artificial nucleotide analogue described herein. In some embodiments, a polynucleic acid molecule of SEQ ID NOs: 16-81 comprises about 8 modifications in which the modifications comprise an artificial nucleotide analogue described herein. In some embodiments, a polynucleic acid molecule of SEQ ID NOs: 16-81 comprises about 9 modifications in which the modifications comprise an artificial nucleotide analogue described herein. In some embodiments, a polynucleic acid molecule of SEQ ID NOs: 16-81 comprises about 10 modifications in which the modifications comprise an artificial nucleotide analogue described herein. In some embodiments, a polynucleic acid molecule of SEQ ID NOs: 16-81 comprises about 11 modifications in which the modifications comprise an artificial nucleotide analogue described herein. In some embodiments, a polynucleic acid molecule of SEQ ID NOs: 16-81 comprises about 12 modifications in which the modifications comprise an artificial nucleotide analogue described herein. In some embodiments, a polynucleic acid molecule of SEQ ID NOs: 16-81 comprises about 13 modifications in which the modifications comprise an artificial nucleotide analogue described herein. In some embodiments, a polynucleic acid molecule of SEQ ID NOs: 16-81 comprises about 14 modifications in which the modifications comprise an artificial nucleotide analogue described herein. In some embodiments, a polynucleic acid molecule of SEQ ID NOs: 16-81 comprises about 15 modifications in which the modifications comprise an artificial nucleotide analogue described herein. In some embodiments, a polynucleic acid molecule of SEQ ID NOs: 16-81 comprises about 16 modifications in which the modifications comprise an artificial nucleotide analogue described herein. In some embodiments, a polynucleic acid molecule of SEQ ID NOs: 16-81 comprises about 17 modifications in which the modifications comprise an artificial nucleotide analogue described herein. In some embodiments, a polynucleic acid molecule of SEQ ID NOs: 16-81 comprises about 18 modifications in which the modifications comprise an artificial nucleotide analogue described herein. In some embodiments, a polynucleic acid molecule of SEQ ID NOs: 16-81 comprises about 19 modifications in which the modifications comprise an artificial nucleotide analogue described herein. In some embodiments, a polynucleic acid molecule of SEQ ID NOs: 16-81 comprises about 20 modifications in which the modifications comprise an artificial nucleotide analogue described herein. In some embodiments, a polynucleic acid molecule of SEQ ID NOs: 16-81 comprises about 21 modifications in which the modifications comprise an artificial nucleotide analogue described herein. In some embodiments, a polynucleic acid molecule of SEQ ID NOs: 16-81 comprises about 22 modifications in which the modifications comprise an artificial nucleotide analogue described herein. In some embodiments, a polynucleic acid molecule of SEQ ID NOs: 16-81 comprises about 23 modifications in which the modifications comprise an artificial nucleotide analogue described herein. In some embodiments, a polynucleic acid molecule of SEQ ID NOs: 16-81 comprises about 24 modifications in which the modifications comprise an artificial nucleotide analogue described herein. In some embodiments, a polynucleic acid molecule of SEQ ID NOs: 16-81 comprises about 25 modifications in which the modifications comprise an artificial nucleotide analogue described herein.

In some instances, a polynucleic acid molecule that comprises an artificial nucleotide analogue comprises a sequence selected from SEQ ID NOs: 46-81.

In some embodiments, a polynucleic acid molecule is assembled from two separate polynucleotides wherein one polynucleotide comprises the sense strand and the second polynucleotide comprises the antisense strand of the polynucleic acid molecule. In other embodiments, the sense strand is connected to the antisense strand via a linker molecule, which in some instances, is a polynucleotide linker or a non-nucleotide linker.

In some embodiments, a polynucleic acid molecule comprises a sense strand and antisense strand, wherein pyrimidine nucleotides in the sense strand comprise 2'-O-methylpyrimidine nucleotides and purine nucleotides in the sense strand comprise 2'-deoxy purine nucleotides. In some embodiments, a polynucleic acid molecule comprises a sense strand and antisense strand, wherein pyrimidine nucleotides present in the sense strand comprise 2'-deoxy-2'-fluoro pyrimidine nucleotides and wherein purine nucleotides present in the sense strand comprise 2'-deoxy purine nucleotides.

In some embodiments, a polynucleic acid molecule comprises a sense strand and antisense strand, wherein the pyrimidine nucleotides when present in said antisense strand are 2'-deoxy-2'-fluoro pyrimidine nucleotides and the purine nucleotides when present in said antisense strand are 2'-O-methyl purine nucleotides.

In some embodiments, a polynucleic acid molecule comprises a sense strand and antisense strand, wherein the pyrimidine nucleotides when present in said antisense strand are 2'-deoxy-2'-fluoro pyrimidine nucleotides and wherein the purine nucleotides when present in said antisense strand comprise 2'-deoxy-purine nucleotides.

In some embodiments, a polynucleic acid molecule comprises a sense strand and antisense strand, wherein the sense strand includes a terminal cap moiety at the 5'-end, the 3'-end, or both of the 5' and 3' ends of the sense strand. In other embodiments, the terminal cap moiety is an inverted deoxy abasic moiety.

In some embodiments, a polynucleic acid molecule comprises a sense strand and an antisense strand, wherein the antisense strand comprises a phosphate backbone modification at the 3' end of the antisense strand. In some instances, the phosphate backbone modification is a phosphorothioate.

In some embodiments, a polynucleic acid molecule comprises a sense strand and an antisense strand, wherein the antisense strand comprises a glyceryl modification at the 3' end of the antisense strand.

In some embodiments, a polynucleic acid molecule comprises a sense strand and an antisense strand, in which the sense strand comprises one or more (for example, about 1, 2, 3, 4, 5, 6, 7, 8, 9, 10, 11, 12, 13, 14, 15, 16, 17, 18, 19, 20, or more) phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or about one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and in which the antisense strand comprises about 1 to about 10 or more, specifically about 1, 2, 3, 4, 5, 6, 7, 8, 9, 10, 11, 12, 13, 14, 15, 16, 17, 18, 19, 20, or more, phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more (for example about 1, 2, 3, 4, 5, 6, 7, 8, 9, 10, or more) pyrimidine nucleotides of the sense and/or antisense strand are chemically-modified with 2'-deoxy, 2'-O-methyl and/or 2'-deoxy-2'-fluoro nucleotides, with or without one or more (for example about 1, 2, 3, 4, 5, 6, 7, 8, 9, 10, or more) phosphorothioate internucleotide linkages and/or a terminal cap molecule at the 3'-end, the 5'-end, or both of the 3'- and 5'-ends, being present in the same or different strand.

In some embodiments, a polynucleic acid molecule comprises a sense strand and an antisense strand, in which the sense strand comprises about 1 to about 25 (for example, about 1, 2, 3, 4, 5, 6, 7, 8, 9, 10, 11, 12, 13, 14, 15, 16, 17, 18, 19, 20, or more) phosphorothioate internucleotide linkages, and/or one or more (e.g., about 1, 2, 3, 4, 5, 6, 7, 8, 9, 10, or more) 2'-deoxy, 2'-O-methyl, 2'-deoxy-2'-fluoro, and/or one or more (e.g., about 1, 2, 3, 4, 5, 6, 7, 8, 9, 10, or more) universal base modified nucleotides, and optionally a terminal cap molecule at the 3-end, the 5'-end, or both of the 3'- and 5'-ends of the sense strand; and in which the antisense strand comprises about 1 to about 25 or more (for example about 1, 2, 3, 4, 5, 6, 7, 8, 9, 10, 11, 12, 13, 14, 15, 16, 17, 18, 19, 20, or more) phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more (for example about 1, 2, 3, 4, 5, 6, 7, 8, 9, 10, or more) pyrimidine nucleotides of the sense and/or antisense strand are chemically-modified with 2'-deoxy, 2'-O-methyl and/or 2'-deoxy-2'-fluoro nucleotides, with or without about 1 to about 25 or more (for example about 1, 2, 3, 4, 5, 6, 7, 8, 9, 10, 11, 12, 13, 14, 15, 16, 17, 18, 19, 20, or more) phosphorothioate internucleotide linkages and/or a terminal cap molecule at the 3'-end, the 5'-end, or both of the 3'- and 5'-ends, being present in the same or different strand.

In some embodiments, a polynucleic acid molecule comprises a sense strand and an antisense strand, in which the antisense strand comprises one or more (for example, about 1, 2, 3, 4, 5, 6, 7, 8, 9, 10, 11, 12, 13, 14, 15, 16, 17, 18, 19, 20, or more) phosphorothioate internucleotide linkages, and/ or about one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10 or more, phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more (for example about 1, 2, 3, 4, 5, 6, 7, 8, 9, 10, 11, 12, 13, 14, 15, 16, 17, 18, 19, 20, or more) pyrimidine nucleotides of the sense and/or antisense strand are chemically-modified with 2'-deoxy, 2'-O-methyl and/or 2'-deoxy-2'-fluoro nucleotides, with or without one or more (for example, about 1, 2, 3, 4, 5, 6, 7, 8, 9, 10 or more) phosphorothioate internucleotide linkages and/ or a terminal cap molecule at the 3'-end, the 5'-end, or both of the 3' and 5'-ends, being present in the same or different strand.

In some embodiments, a polynucleic acid molecule comprises a sense strand and an antisense strand, in which the antisense strand comprises about 1 to about 25 or more (for example, about 1, 2, 3, 4, 5, 6, 7, 8, 9, 10, 11, 12, 13, 14, 15, 16, 17, 18, 19, 20, or more) phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 25 or more (for example about 1, 2, 3, 4, 5, 6, 7, 8, 9, 10, 11, 12, 13, 14, 15, 16, 17, 18, 19, 20, or more) phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more (for example about 1, 2, 3, 4, 5, 6, 7, 8, 9, 10 or more) pyrimidine nucleotides of the sense and/or antisense strand are chemically-modified with 2'-deoxy, 2'-O-methyl and/or 2'-deoxy-2'-fluoro nucleotides, with or without about 1 to about 5 (for example about 1, 2, 3, 4, 5 or more) phosphorothioate internucleotide linkages and/or a terminal cap molecule at the 3'-end, the 5'-end, or both of the 3'- and 5'-ends, being present in the same or different strand.

In some embodiments, a polynucleic acid molecule described herein is a chemically-modified short interfering nucleic acid molecule having about 1 to about 25 (for example, about 1, 2, 3, 4, 5, 6, 7, 8, 9, 10, 11, 12, 13, 14, 15, 16, 17, 18, 19, 20 or more) phosphorothioate internucleotide linkages in each strand of the polynucleic acid molecule.

In another embodiment, a polynucleic acid molecule described herein comprises 2'-5' internucleotide linkages. In some instances, the 2'-5' internucleotide linkage(s) is at the 3'-end, the 5'-end, or both of the 3'- and 5'-ends of one or both sequence strands. In addition instances, the 2'-5' internucleotide linkage(s) is present at various other positions within one or both sequence strands (for example, about 1, 2, 3, 4, 5, 6, 7, 8, 9, 10, or more) including every internucleotide linkage of a pyrimidine nucleotide in one or both strands of the polynucleic acid molecule comprise a 2'-5' internucleotide linkage, or about 1, 2, 3, 4, 5, 6, 7, 8, 9, 10, or more, including every internucleotide linkage of a purine nucleotide in one or both strands of the polynucleic acid molecule comprise a 2'-5' internucleotide linkage.

In some embodiments, a polynucleic acid molecule is a single stranded polynucleic acid molecule that mediates RNAi activity in a cell or reconstituted in vitro system, wherein the polynucleic acid molecule comprises a single stranded polynucleotide having complementarily to a target nucleic acid sequence, and wherein one or more pyrimidine nucleotides present in the polynucleic acid are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein one or more purine nucleotides present in the polynucleic acid are 2'-deoxy purine nucleotides (e.g., wherein all purine nucleotides are 2'-deoxy purine nucleotides or alternately a plurality of purine nucleotides are 2'-deoxy purine nucleotides), and a terminal cap modification, that is optionally present at the 3'-end, the 5'-end, or both of the 3' and 5'-ends of the antisense sequence, the polynucleic acid molecule optionally further comprising about 1 to about 4 (e.g., about 1, 2, 3, or 4) terminal 2'-deoxynucleotides 3'-end of the polynucleic acid molecule, wherein the terminal nucleotides further comprise one or more (e.g., 1, 2, 3, or 4) phosphorothioate internucleotide linkages, and wherein the polynucleic acid molecule optionally further comprises a terminal phosphate group, such as a 5'-terminal phosphate group.

In some cases, one or more of the artificial nucleotide analogues described herein are resistant toward nucleases such as for example ribonuclease such as RNase H, deoxyribunuclease such as DNase, or exonuclease such as 5'-3' exonuclease and 3'-5' exonuclease, when compared to natural polynucleic acid molecules. In some instances, artificial nucleotide analogues comprising 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribunuclease such as DNase, or exonuclease such as 5'-3' exonuclease and 3'-5' exonuclease. In some instances, 2'-O-methyl modified polynucleic acid molecule is nuclease resistant (e.g., RNase H, DNase, 5'-3' exonuclease or 3'-5' exonuclease resistant). In some instances, 2'O-methoxyethyl (2'-O-MOE) modified polynucleic acid molecule is nuclease resistant (e.g., RNase H, DNase, 5'-3' exonuclease or 3'-5' exonuclease resistant). In some instances, 2'-O-aminopropyl modified polynucleic acid molecule is nuclease resistant (e.g., RNase H, DNase, 5'-3' exonuclease or 3'-5' exonuclease resistant). In some instances, 2'-deoxy modified polynucleic acid molecule is nuclease resistant (e.g., RNase H, DNase, 5'-3' exonuclease or 3'-5' exonuclease resistant). In some instances, T-deoxy-2'-fluoro modified polynucleic acid molecule is nuclease resistant (e.g., RNase H, DNase, 5'-3' exonuclease or 3'-5' exonuclease resistant). In some instances, 2'-O-aminopropyl (2'-O-AP) modified polynucleic acid molecule is nuclease resistant (e.g., RNase H, DNase, 5'-3' exonuclease or 3'-5' exonuclease resistant). In some instances, 2'-O-dimethylaminoethyl (2'-O-DMAOE) modified polynucleic acid molecule is nuclease resistant (e.g., RNase H, DNase, 5'-3' exonuclease or 3'-5' exonuclease resistant). In some instances, 2'-O-dimethylaminopropyl (2'-O-DMAP) modified polynucleic acid molecule is nuclease resistant (e.g., RNase H, DNase, 5'-3' exonuclease or 3'-5' exonuclease resistant). In some instances, T-O-dimethylaminoethyloxyethyl (2'-O-DMAEOE) modified polynucleic acid molecule is nuclease resistant (e.g., RNase H, DNase, 5'-3' exonuclease or 3'-5' exonuclease resistant). In some instances, 2'-O—N-methylacetamido (2'-O-NMA) modified polynucleic acid molecule is nuclease resistant (e.g., RNase H, DNase, 5'-3' exonuclease or 3'-5' exonuclease resistant). In some instances, LNA modified polynucleic acid molecule is nuclease resistant (e.g., RNase H, DNase, 5'-3' exonuclease or 3'-5' exonuclease resistant). In some instances, ENA modified polynucleic acid molecule is nuclease resistant (e.g., RNase H, DNase, 5'-3' exonuclease or 3'-5' exonuclease resistant). In some instances, HNA modified polynucleic acid molecule is nuclease resistant (e.g., RNase H, DNase, 5'-3' exonuclease or 3'-5' exonuclease resistant). In some instances, morpholinos is nuclease resistant (e.g., RNase H, DNase, 5'-3' exonuclease or 3'-5' exonuclease resistant). In some instances, PNA modified polynucleic acid molecule is resistant to nucleases (e.g., RNase H, DNase, 5'-3' exonuclease or 3'-5' exonuclease resistant). In some instances, methylphosphonate nucleotides modified polynucleic acid molecule is nuclease resistant (e.g., RNase H, DNase, 5'-3' exonuclease or 3'-5' exonuclease resistant). In some instances, thiolphosphonate nucleotides modified polynucleic acid molecule is nuclease resistant (e.g., RNase H, DNase, 5'-3' exonuclease or 3'-5' exonuclease resistant). In some instances, polynucleic acid molecule comprising 2'-fluoro N3-P5'-phosphoramidites is nuclease resistant (e.g., RNase H, DNase, 5'-3' exonuclease or 3'-5' exonuclease resistant). In some instances, the 5' conjugates described herein inhibit 5'-3' exonucleolytic cleavage. In some instances, the 3' conjugates described herein inhibit 3'-5" exonucleolytic cleavage.

In some embodiments, one or more of the artificial nucleotide analogues described herein have increased binding affinity toward their mRNA target relative to an equivalent natural polynucleic acid molecule. The one or more of the artificial nucleotide analogues comprising 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, or 2'-fluoro N3-P5'-phosphoramidites have increased binding affinity toward their mRNA target relative to an equivalent natural polynucleic acid molecule. In some instances, 2'-O-methyl-modified polynucleic acid molecule has increased binding affinity toward their mRNA target relative to an equivalent natural polynucleic acid molecule. In some instances, 2'-O-methoxyethyl (2'-O-MOE) modified polynucleic acid molecule has increased binding affinity toward their mRNA target relative to an equivalent natural polynucleic acid molecule. In some instances, 2'-O-aminopropyl modified polynucleic acid molecule has increased binding affinity toward their mRNA target relative to an equivalent natural polynucleic acid molecule. In some instances, 2'-deoxy modified polynucleic acid molecule has increased binding affinity toward their mRNA target relative to an equivalent natural polynucleic acid molecule. In some instances, T-deoxy-2'-fluoro modified polynucleic acid molecule has increased binding affinity toward their mRNA target relative to an equivalent natural polynucleic acid molecule. In some instances, 2'-O-aminopropyl (2'-O-AP) modified polynucleic acid molecule has increased binding affinity toward their mRNA target relative to an equivalent natural polynucleic acid molecule. In some instances, 2'-O-dimethylaminoethyl (2'-O-DMAOE) modified polynucleic acid molecule has increased binding affinity toward their mRNA target relative to an equivalent natural polynucleic acid molecule. In some instances, 2'-O-dimethylaminopropyl (2'-O-DMAP) modified polynucleic acid molecule has increased binding affinity toward their mRNA target relative to an equivalent natural polynucleic acid molecule. In some instances, T-O-dimethylaminoethyloxyethyl (2'-O-DMAEOE) modified polynucleic acid molecule has increased binding affinity toward their mRNA target relative to an equivalent natural polynucleic acid molecule. In some instances, 2'-O—N-methylacetamido (2'-O-NMA) modified polynucleic acid molecule has increased binding affinity toward their mRNA target relative to an equivalent natural polynucleic acid molecule. In some instances, LNA-modified polynucleic acid molecule has increased binding affinity toward their mRNA target relative to an equivalent natural polynucleic acid molecule. In some instances, ENA-modified polynucleic acid molecule has increased binding affinity toward their mRNA target relative to an equivalent natural polynucleic acid molecule. In some instances, PNA-modified polynucleic acid molecule has increased binding affinity toward their mRNA target relative to an equivalent natural polynucleic acid molecule. In some instances, HNA-modified polynucleic acid molecule has increased binding affinity toward their mRNA target relative to an equivalent natural polynucleic acid molecule. In some instances, morpholino-modified polynucleic acid molecule has increased binding affinity toward their mRNA target relative to an equivalent natural polynucleic acid molecule. In some instances, methylphosphonate nucleotide-modified polynucleic acid molecule has increased binding affinity toward their mRNA target relative to an equivalent natural polynucleic acid molecule. In some instances, thiolphosphonate nucleotide-modified polynucleic acid molecule has increased binding affinity toward their mRNA target relative to an equivalent natural polynucleic acid molecule. In some instances, polynucleic acid molecule comprising 2'-fluoro N3-P5'-phosphoramidites has increased binding affinity toward their mRNA target relative to an equivalent natural polynucleic acid molecule. In some cases, the increased affinity is illustrated with a lower Kd, a higher melt temperature (Tm), or a combination thereof.

In some embodiments, a polynucleic acid molecule described herein is a chirally pure (or stereo pure) polynucleic acid molecule, or a polynucleic acid molecule comprising a single enantiomer. In some instances, the polynucleic acid molecule comprises L-nucleotide. In some instances, the polynucleic acid molecule comprises D-nucleotides. In some instance, a polynucleic acid molecule composition comprises less than 30%, 25%, 20%, 15%, 10%, 5%, 4%, 3%, 2%, 1%, or less of its mirror enantiomer. In some cases, a polynucleic acid molecule composition comprises less than 30%, 25%, 20%, 15%, 10%, 5%, 4%, 3%, 2%, 1%, or less of a racemic mixture. In some instances, the polynucleic acid molecule is a polynucleic acid molecule described in: U.S. Patent Publication Nos: 2014/194610 and 2015/211006; and PCT Publication No.: WO2015107425.

In some embodiments, a polynucleic acid molecule described herein is further modified to include an aptamer-conjugating moiety. In some instances, the aptamer conjugating moiety is a DNA aptamer-conjugating moiety. In some instances, the aptamer-conjugating moiety is Alphamer (Centauri Therapeutics), which comprises an aptamer portion that recognizes a specific cell-surface target and a portion that presents a specific epitopes for attaching to circulating antibodies. In some instance, a polynucleic acid molecule described herein is further modified to include an aptamer-conjugating moiety as described in: U.S. Pat. Nos: 8,604,184, 8,591,910, and 7,850,975.

In additional embodiments, a polynucleic acid molecule described herein is modified to increase its stability. In some embodiment, the polynucleic acid molecule is RNA (e.g., siRNA), and the polynucleic acid molecule is modified to increase its stability. In some instances, the polynucleic acid molecule is modified by one or more of the modifications described above to increase its stability. In some cases, the polynucleic acid molecule is modified at the 2' hydroxyl position, such as by 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modification or by a locked or bridged ribose conformation (e.g., LNA or ENA). In some cases, the polynucleic acid molecule is modified by 2'-O-methyl and/or 2'-O-methoxyethyl ribose. In some cases, the polynucleic acid molecule also includes morpholinos, PNAs, HNA, methylphosphonate nucleotides, thiolphosphonate nucleotides, and/or 2'-fluoro N3-P5'-phosphoramidites to increase its stability. In some instances, the polynucleic acid molecule is a chirally pure (or stereo pure) polynucleic acid molecule. In some instances, the chirally pure (or stereo pure) polynucleic acid molecule is modified to increase its stability. Suitable modifications to the RNA to increase stability for delivery will be apparent to the skilled person.

In some embodiments, a polynucleic acid molecule describe herein has RNAi activity that modulates expression of RNA encoded by KRAS. In some instances, a polynucleic acid molecule described herein is a double-stranded siRNA molecule that down-regulates expression of KRAS, wherein one of the strands of the double-stranded siRNA molecule comprises a nucleotide sequence that is complementary to a nucleotide sequence of KRAS or RNA encoded by KRAS or a portion thereof, and wherein the second strand of the double-stranded siRNA molecule comprises a nucleotide sequence substantially similar to the nucleotide sequence of KRAS or RNA encoded by KRAS or a portion thereof. In some cases, a polynucleic acid molecule described herein is a double-stranded siRNA molecule that down-regulates expression of KRAS, wherein each strand of the siRNA molecule comprises about 15 to 25, 18 to 24, or 19 to about 23 nucleotides, and wherein each strand comprises at least about 14, 17, or 19 nucleotides that are complementary to the nucleotides of the other strand. In some cases, a polynucleic acid molecule described herein is a double-stranded siRNA molecule that down-regulates expression of KRAS, wherein each strand of the siRNA molecule comprises about 19 to about 23 nucleotides, and wherein each strand comprises at least about 19 nucleotides that are complementary to the nucleotides of the other strand. In some instances, the RNAi activity occurs within a cell. In other instances, the RNAi activity occurs in a reconstituted in vitro system.

In some embodiments, a polynucleic acid molecule describe herein has RNAi activity that modulates expression of RNA encoded by KRAS. In some instances, a polynucleic acid molecule described herein is a single-stranded siRNA molecule that down-regulates expression of KRAS, wherein the single-stranded siRNA molecule comprises a nucleotide sequence that is complementary to a nucleotide sequence of KRAS or RNA encoded by KRAS or a portion thereof. In some cases, a polynucleic acid molecule described herein is a single-stranded siRNA molecule that down-regulates expression of KRAS, wherein the siRNA molecule comprises about 15 to 25, 18 to 24, or 19 to about 23 nucleotides. In some cases, a polynucleic acid molecule described herein is a single-stranded siRNA molecule that down-regulates expression of KRAS, wherein the siRNA molecule comprises about 19 to about 23 nucleotides. In some instances, the RNAi activity occurs within a cell. In other instances, the RNAi activity occurs in a reconstituted in vitro system.

In some instances, a polynucleic acid molecule is a double-stranded polynucleotide molecule comprising self-complementary sense and antisense regions, wherein the antisense region comprises a nucleotide sequence that is complementary to a nucleotide sequence in a target nucleic acid molecule or a portion thereof and the sense region has a nucleotide sequence corresponding to the target nucleic acid sequence or a portion thereof. In some instances, the polynucleic acid molecule is assembled from two separate polynucleotides, where one strand is the sense strand and the other is the antisense strand, wherein the antisense and sense strands are self-complementary (e.g., each strand comprises a nucleotide sequence that is complementary to the nucleotide sequence in the other strand; such as where the antisense strand and sense strand form a duplex or double-stranded structure, for example wherein the double-stranded region is about 19, 20, 21, 22, 23, or more base pairs); the antisense strand comprises a nucleotide sequence that is complementary to a nucleotide sequence in a target nucleic acid molecule or a portion thereof and the sense strand comprises a nucleotide sequence corresponding to the target nucleic acid sequence or a portion thereof. Alternatively, the polynucleic acid molecule is assembled from a single oligonucleotide, where the self-complementary sense and antisense regions of the polynucleic acid molecule are linked by means of a nucleic acid based or non-nucleic acid-based linker(s).

In some cases, a polynucleic acid molecule is a polynucleotide with a duplex, asymmetric duplex, hairpin, or asymmetric hairpin secondary structure, having self-complementary sense and antisense regions, wherein the antisense region comprises a nucleotide sequence that is complementary to a nucleotide sequence in a separate target nucleic acid molecule or a portion thereof and the sense region has a nucleotide sequence corresponding to the target nucleic acid sequence or a portion thereof. In other cases, the polynucleic acid molecule is a circular single-stranded polynucleotide having two or more loop structures and a stem comprising self-complementary sense and antisense regions, wherein the antisense region comprises a nucleotide sequence that is complementary to a nucleotide sequence in a target nucleic acid molecule or a portion thereof and the sense region has a nucleotide sequence corresponding to the target nucleic acid sequence or a portion thereof, and wherein the circular polynucleotide is processed either in vivo or in vitro to generate an active polynucleic acid molecule capable of mediating RNAi. In additional cases, the polynucleic acid molecule also comprises a single-stranded polynucleotide having a nucleotide sequence complementary to a nucleotide sequence in a target nucleic acid molecule or a portion thereof (for example, where such polynucleic acid molecule does not require the presence within the polynucleic acid molecule of a nucleotide sequence corresponding to the target nucleic acid sequence or a portion thereof), wherein the single stranded polynucleotide further comprises a terminal phosphate group, such as a 5'-phosphate (see for example Martinez et al., 2002, *Cell*, 110, 563-574 and Schwarz et al., 2002, *Molecular Cell*, 10, 537-568), or 5',3'-diphosphate.

In some instances, an asymmetric duplex is a linear polynucleic acid molecule comprising an antisense region, a loop portion that comprises nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin polynucleic acid molecule comprises an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. In some cases, the asymmetric hairpin polynucleic acid molecule also comprises a 5'-terminal phosphate group that is chemically modified. In additional cases, the loop portion of the asymmetric hairpin polynucleic acid molecule comprises nucleotides, non-nucleotides, linker molecules, or conjugate molecules.

In some embodiments, an asymmetric duplex is a polynucleic acid molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex polynucleic acid molecule comprises an antisense region having length sufficient to mediate RNAi in a cell or in vitro system (e.g. about 19 to about 22 nucleotides) and a sense region having about 3 to about 18 nucleotides that are complementary to the antisense region.

In some cases, a universal base refers to nucleotide base analogs that form base pain with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole 5-nitroindole, and 6-nitroindole as known in the art (see for example Loakes, 2001, *Nucleic Acids Research*, 29, 2437-2447).

Polynucleic Acid Molecule Synthesis

In some embodiments, a polynucleic acid molecule described herein is constructed using chemical synthesis and/or enzymatic ligation reactions using procedures known in the art. For example, a polynucleic acid molecule is chemically synthesized using naturally occurring nucleotides or variously modified nucleotides designed to increase the biological stability of the molecules or to increase the physical stability of the duplex formed between the polynucleic acid molecule and target nucleic acids. Exemplary methods include those described in: U.S. Pat. Nos. 5,142,047; 5,185,444; 5,889,136; 6,008,400; and 6,111,086; PCT Publication No. WO2009099942; or European Publication No. 1579015. Additional exemplary methods include those described in: Griffey et al., "2'-O-aminopropyl ribonucleotides: a zwitterionic modification that enhances the exonuclease resistance and biological activity of antisense oligonucleotides," *J. Med. Chem.* 39(26):5100-5109 (1997)); Obika, et al. "Synthesis of 2'-O,4'-C-methyleneuridine and -cytidine. Novel bicyclic nucleosides having a fixed C3,-endo sugar puckering". *Tetrahedron Letters* 38 (50): 8735 (1997); Koizumi, M. "ENA oligonucleotides as therapeutics". *Current opinion in molecular therapeutics* 8 (2): 144-149 (2006); and Abramova et al., "Novel oligonucleotide analogues based on morpholino nucleoside subunits-antisense technologies: new chemical possibilities," Indian Journal of Chemistry 48B:1721-1726 (2009). Alternatively, the polynucleic acid molecule is produced biologically using an expression vector into which a polynucleic acid molecule has been subcloned in an antisense orientation (i.e., RNA transcribed from the inserted polynucleic acid molecule will be of an antisense orientation to a target polynucleic acid molecule of interest).

In some embodiments, a polynucleic acid molecule is synthesized via a tandem synthesis methodology, wherein both strands are synthesized as a single contiguous oligonucleotide fragment or strand separated by a cleavable linker which is subsequently cleaved to provide separate fragments or strands that hybridize and permit purification of the duplex.

In some instances, a polynucleic acid molecule is assembled from two distinct nucleic acid strands or fragments wherein one fragment includes the sense region and the second fragment includes the antisense region of the molecule.

Additional modification methods for incorporating, for example, sugar, base, and phosphate modifications include: Eckstein et al., International Publication PCT No. WO 92/07065; Perrault et al. *Nature*, 1990, 344, 565-568; Pieken et al. *Science*, 1991, 253, 314-317; Usman and Cedergren, *Trends in Biochem. Sci.*, 1992, 17, 334-339; Usman et al. International Publication PCT No. WO 93/15187; Sproat, U.S. Pat. No. 5,334,711 and Beigelman et al., 1995, *J. Biol. Chem.*, 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.*, 39, 1131; Earnshaw and Gait, 1998, *Biopolymers (Nucleic Acid Sciences)*, 48, 39-55; Verma and Eckstein, 1998, *Annu. Rev. Biochem.*, 67, 99-134; and Burlina et al., 1997, *Bioorg. Med. Chem.*, 5, 1999-2010. Such publications describe general methods and strategies to determine the location of incorporation of sugar, base, and/or phosphate modifications and the like into nucleic acid molecules without modulating catalysis.

In some instances, while chemical modification of the polynucleic acid molecule internucleotide linkages with phosphorothioate, phosphorodithioate, and/or 5'-methylphosphonate linkages improves stability, excessive modifications sometimes cause toxicity or decreased activity. Therefore, when designing nucleic acid molecules, the amount of these internucleotide linkages in some cases is minimized. In such cases, the reduction in the concentration of these linkages lowers toxicity, and increases efficacy and specificity of these molecules.

Diseases

In some embodiments, a polynucleic acid molecule or a pharmaceutical composition described herein is used for the treatment of a disease or disorder. In some instances, the disease or disorder is a cancer. In some embodiments, a polynucleic acid molecule or a pharmaceutical composition described herein is used for the treatment of cancer. In some instances, the cancer is a solid tumor. In some instances, the cancer is a hematologic malignancy. In some instances, the cancer is a relapsed or refractory cancer, or a metastatic cancer. In some instances, the solid tumor is a relapsed or refractory solid tumor, or a metastatic solid tumor. In some cases, the hematologic malignancy is a relapsed or refractory hematologic malignancy, or a metastatic hematologic malignancy.

In some embodiments, the cancer is a solid tumor. Exemplary solid tumor includes, but is not limited to, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

In some instances, a polynucleic acid molecule or a pharmaceutical composition described herein is used for the treatment of a solid tumor. In some instances, a polynucleic acid molecule or a pharmaceutical composition described herein is used for the treatment of anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer. In some instances, the solid tumor is a relapsed or refractory solid tumor, or a metastatic solid tumor.

In some instances, the cancer is a hematologic malignancy. In some instances, the hematologic malignancy is a leukemia, a lymphoma, a myeloma, a non-Hodgkin's lymphoma, or a Hodgkin's lymphoma. In some instances, the hematologic malignancy comprises chronic lymphocytic leukemia (CLL), small lymphocytic lymphoma (SLL), high risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenström's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, a polynucleic acid molecule or a pharmaceutical composition described herein is used for the treatment of a hematologic malignancy. In some instances, a polynucleic acid molecule or a pharmaceutical composition described herein is used for the treatment of a leukemia, a lymphoma, a myeloma, a non-Hodgkin's lymphoma, or a Hodgkin's lymphoma. In some instances, the hematologic malignancy comprises chronic lymphocytic leukemia (CLL), small lymphocytic lymphoma (SLL), high risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenström's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some cases, the hematologic malignancy is a relapsed or refractory hematologic malignancy, or a metastatic hematologic malignancy.

In some instances, the cancer is a KRAS-associated cancer. In some instances, a polynucleic acid molecule or a pharmaceutical composition described herein is used for the treatment of a KRAS-associated cancer. In some instances, the cancer is a solid tumor. In some instances, the cancer is a hematologic malignancy. In some instances, the solid tumor is a relapsed or refractory solid tumor, or a metastatic solid tumor. In some cases, the hematologic malignancy is a relapsed or refractory hematologic malignancy, or a metastatic hematologic malignancy. In some instances, the cancer comprises bladder cancer, breast cancer, colorectal cancer, endometrial cancer, esophageal cancer, glioblastoma multiforme, head and neck cancer, kidney cancer, lung cancer, ovarian cancer, pancreatic cancer, prostate cancer, thyroid cancer, acute myeloid leukemia, CLL, DLBCL, or multiple myeloma.

Pharmaceutical Formulation

In some embodiments, the pharmaceutical formulations described herein are administered to a subject by multiple administration routes including, but not limited to, parenteral (e.g., intravenous, subcutaneous, intramuscular), oral, intranasal, buccal, rectal, or transdermal administration routes. In some instances, the pharmaceutical composition describe herein is formulated for parenteral (e.g., intravenous, subcutaneous, intramuscular) administration. In other instances, the pharmaceutical composition describe herein is formulated for oral administration. In still other instances, the pharmaceutical composition describe herein is formulated for intranasal administration.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate- and controlled-release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes, and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety described herein). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin, dextrin, or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety described herein is conjugated either directly or indirectly to the nanoparticle. In some instances, at least 1, 5, 10, 15, 20, 30, 40, 50, 60, 70, 80, 90, 100 or more polynucleic acid molecules or binding moieties described herein are conjugated either directly or indirectly to a nanoparticle.

In some embodiments, the pharmaceutical formulation comprise a delivery vector, e.g., a recombinant vector, for the delivery of the polynucleic acid molecule into cells. In some instances, the recombinant vector is DNA plasmid. In other instances, the recombinant vector is a viral vector. Exemplary viral vectors include vectors derived from adeno-associated virus, retrovirus, adenovirus, or alphavirus. In some instances, the recombinant vectors capable of expressing the polynucleic acid molecules provide stable expression in target cells. In additional instances, viral vectors are used that provide for transient expression of polynucleic acid molecules.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

In some instances, the pharmaceutical formulations further include pH-adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate, and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulations further include diluent which are used to stabilize compounds because they provide a more stable environment. Salts dissolved in buffered solutions (which also provide pH control or maintenance) are utilized as diluents in the art, including, but not limited to a phosphate-buffered saline solution. In certain instances, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulo se acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some cases, the pharmaceutical formulations include disintegration agents or disintegrants to facilitate the breakup or disintegration of a substance. The term "disintegrate" includes both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone, alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing, or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™ sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, dimethyl isosorbide, and the like.

Stabilizers include compounds such as any antioxidation agents, buffers, acids, preservatives, and the like.

Suspending agents include compounds such as polyvinylpyrrolidone (e.g., polyvinylpyrrolidone K12, polyvinylpyrrolidone K17, polyvinylpyrrolidone K25, or polyvinylpyrrolidone K30), vinyl pyrrolidone/vinyl acetate copolymer (S630), polyethylene glycol (e.g., the polyethylene glycol has a molecular weight of about 300 to about 6000, or about 3350 to about 4000, or about 7000 to about 5400), sodium carboxymethylcellulose, methylcellulose, hydroxypropylmethylcellulose, hydroxymethylcellulose acetate stearate, polysorbate-80, hydroxyethylcellulose, sodium alginate, gums (such as, e.g., gum tragacanth and gum acacia, guar gum, xanthans, including xanthan gum), sugars, cellulosics (such as, e.g., sodium carboxymethylcellulose, methylcellulo se, sodium carboxymethylcellulose, hydroxypropylmethylcellulose, hydroxyethylcellulose), polysorbate-80, sodium alginate, polyethoxylated sorbitan monolaurate, polyethoxylated sorbitan monolaurate, povidone, and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants are included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans, and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts, and the like.

Therapeutic Regimens

In some embodiments, the pharmaceutical compositions described herein are administered for therapeutic applications. In some embodiments, the pharmaceutical composition is administered once per day, twice per day, three times per day, or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some embodiments, two or more different pharmaceutical compositions are coadministered. In some instances, the two or more different pharmaceutical compositions are coadministered simultaneously. In some cases, the two or more different pharmaceutical compositions are coadministered sequentially without a gap of time between administrations. In other cases, the two or more different pharmaceutical compositions are coadministered sequentially with a gap of about 0.5 hour, 1 hour, 2 hour, 3 hour, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, are optionally reduced, as a function of the symptoms, to a level at which the improved disease, disorder or condition is retained.

In some embodiments, the amount of a given agent that corresponds to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in humans. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include KRAS nucleic acid molecule described herein. Such kits optionally include an identifying description or label or instructions relating to its use in the methods described herein.

A kit typically includes labels listing contents and/or instructions for use and package inserts with instructions for use. A set of instructions will also typically be included.

In one embodiment, a label is on or associated with the container. In one embodiment, a label is on a container when letters, numbers, or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the general description and the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that is expected to be within experimental error, e.g., ±5%, ±10%, or ±15%.

The section headings used herein are for organizational purposes only and are not to be construed as limiting the subject matter described.

As used herein, the terms "individual(s)," "subject(s)," and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly, or a hospice worker).

EXAMPLES

These examples are provided for illustrative purposes only and not to limit the scope of the claims provided herein.

Example 1. Sequences

Table 1 illustrates KRAS target sequences. Tables 2 and 3 illustrate polynucleic acid molecule sequences described herein.

TABLE 1

KRAS Target Sequences

| Id # | sequence position in NM_033360.2 | target site in NM_033360.2 | SEQ ID NO: |
|---|---|---|---|
| 182 | 182-200 | AAAUGACUGAAUAUAAACUUGUG | 1 |
| 183 | 183-201 | AAUGACUGAAUAUAAACUUGUGG | 2 |
| 197 | 197-215 | AACUUGUGGUAGUUGGAGCUGGU | 3 |
| 224 | 224-242 | UAGGCAAGAGUGCCUUGACGAUA | 4 |
| 226 | 226-244 | GGCAAGAGUGCCUUGACGAUACA | 5 |

TABLE 1-continued

KRAS Target Sequences

| Id # | sequence position in NM_033360.2 | target site in NM_033360.2 | SEQ ID NO: |
|---|---|---|---|
| 227 | 227-245 | GCAAGAGUGCCUUGACGAUACAG | 6 |
| 228 | 228-246 | CAAGAGUGCCUUGACGAUACAGC | 7 |
| 232 | 232-250 | AGUGCCUUGACGAUACAGCUAAU | 8 |
| 233 | 233-251 | GUGCCUUGACGAUACAGCUAAUU | 9 |
| 236 | 236-254 | CCUUGACGAUACAGCUAAUUCAG | 10 |
| 237 | 237-255 | CUUGACGAUACAGCUAAUUCAGA | 11 |
| 245 | 245-263 | UACAGCUAAUUCAGAAUCAUUUU | 12 |
| 266 | 266-284 | UUGUGGACGAAUAUGAUCCAACA | 13 |
| 269 | 269-287 | UGGACGAAUAUGAUCCAACAAUA | 14 |
| 270 | 270-288 | GGACGAAUAUGAUCCAACAAUAG | 15 |

TABLE 2

KRAS siRNA sequences

| Id # | sequence position in NM_033360.2 | sense strand sequence (5'-3') | SEQ ID NO: | antisense sequence (5'-3') | SEQ ID NO: |
|---|---|---|---|---|---|
| 182 | 182-200 | AUGACUGAAUAUAAACUUGTT | 16 | CAAGUUUAUAUUCAGUCAUTT | 17 |
| 183 | 183-201 | UGACUGAAUAUAAACUUGUTT | 18 | ACAAGUUUAUAUUCAGUCATT | 19 |
| 197 | 197-215 | CUUGUGGUAGUUGGAGCUGTT | 20 | CAGCUCCAACUACCACAAGTT | 21 |
| 224 | 224-242 | GGCAAGAGUGCCUUGACGATT | 22 | UCGUCAAGGCACUCUUGCCTT | 23 |
| 226 | 226-244 | CAAGAGUGCCUUGACGAUATT | 24 | UAUCGUCAAGGCACUCUUGTT | 25 |
| 227 | 227-245 | AAGAGUGCCUUGACGAUACTT | 26 | GUAUCGUCAAGGCACUCUUTT | 27 |
| 228 | 228-246 | AGAGUGCCUUGACGAUACATT | 28 | UGUAUCGUCAAGGCACUCUTT | 29 |
| 232 | 232-250 | UGCCUUGACGAUACAGCUATT | 30 | UAGCUGUAUCGUCAAGGCATT | 31 |
| 233 | 233-251 | GCCUUGACGAUACAGCUAATT | 32 | UUAGCUGUAUCGUCAAGGCTT | 33 |
| 236 | 236-254 | UUGACGAUACAGCUAAUUCTT | 34 | GAAUUAGCUGUAUCGUCAATT | 35 |
| 237 | 237-255 | UGACGAUACAGCUAAUUCATT | 36 | UGAAUUAGCUGUAUCGUCATT | 37 |
| 245 | 245-263 | CAGCUAAUUCAGAAUCAUUTT | 38 | AAUGAUUCUGAAUUAGCUGTT | 39 |
| 266 | 266-284 | GUGGACGAAUAUGAUCCAATT | 40 | UUGGAUCAUAUUCGUCCACTT | 41 |
| 269 | 269-287 | GACGAAUAUGAUCCAACAATT | 42 | UUGUUGGAUCAUAUUCGUCTT | 43 |
| 270 | 270-288 | ACGAAUAUGAUCCAACAAUTT | 44 | AUUGUUGGAUCAUAUUCGUTT | 45 |

TABLE 3

KRAS siRNA Sequences with Chemical Modification

| Id # | sequence position in NM_033360.2 | siRNA sequence with chemical modification sense strand sequence (5'-3') | SEQ ID NO: | siRNA sequence with chemical modification antisense strand sequence (5'-3') | SEQ ID NO: |
|---|---|---|---|---|---|
| 182 | 182-200 | auGfaCfuGfaAfuAfuAfaAfaAfcUfuGfdTsdT | 46 | CfAfaGfuUfuAfuAfuUfcAfgUfcAfudTsdT | 47 |
| 183 | 183-201 | ugAfcUfgAfaUfaUfaAfaCfuUfgUfdTsdT | 48 | AfCfaAfgUfuUfaUfaUfuCfaGfuCfadTsdT | 49 |
| 197 | 197-215 | cuUfgUfgGfuAfgUfuGfgAfgCfuGfdTsdT | 50 | CfAfgCfuCfcAfaCfuAfcCfaCfaAfgdTsdT | 51 |
| 224 | 224-242 | ggCfaAfgAfgUfgCfcUfuGfaCfgAfdTsdT | 52 | UfCfgUfcAfaGfgCfaCfuCfuUfgCfcdTsdT | 53 |
| 226 | 226-244 | caAfgAfgUfgCfcUfuGfaCfgAfuAfdTsdT | 54 | UfAfuCfgUfcAfaGfgCfaCfuCfuUfgdTsdT | 55 |
| 227 | 227-245 | aaGfaGfuGfcCfuUfgAfcGfaUfaCfdTsdT | 56 | GfUfaUfcGfuCfaAfgGfcAfcUfcUfudTsdT | 57 |
| 228 | 228-246 | agAfgUfgCfcUfuGfaCfgAfuAfcAfdTsdT | 58 | UfGfuAfuCfgUfcAfaGfgCfaCfuCfudTsdT | 59 |

TABLE 3-continued

KRAS siRNA Sequences with Chemical Modification

| sequence Id # | sequence position in NM_033360.2 | siRNA sequence with chemical modification sense strand sequence (5'-3') | SEQ ID NO: | siRNA sequence with chemical modification antisense strand sequence (5'-3') | SEQ ID NO: |
|---|---|---|---|---|---|
| 232 | 232-250 | ugCfcUfuGfaCfgAfuAf cAfgCfuAfdTsdT | 60 | UfAfgCfuGfuAfuCfgUfcAfaGf gCfadTsdT | 61 |
| 233 | 233-251 | gcCfuUfgAfcGfaUfaCf aGfcUfaAfdTsdT | 62 | UfUfaGfcUfgUfaUfcGfuCfaAf gGfcdTsdT | 63 |
| 236 | 236-254 | uuGfaCfgAfuAfcAfgCf uAfaUfuCfdTsdT | 64 | GfAfaUfuAfgCfuGfuAfuCfgU fcAfadTsdT | 65 |
| 237 | 237-255 | ugAfcGfaUfaCfaGfcUf aAfuUfcAfdTsdT | 66 | UfGfaAfuUfaGfcUfgUfaUfcGf uCfadTsdT | 67 |
| 245 | 245-263 | caGfcUfaAfuUfcAfgAf aUfcAfuUfdTsdT | 68 | AfAfuGfaUfuCfuGfaAfuUfaGf cUfgdTsdT | 69 |
| 266 | 266-284 | guGfgAfcGfaAfuAfuGf aUfcCfaAfdTsdT | 70 | UfUfgGfaUfcAfuAfuUfcGfuCf cAfcdTsdT | 71 |
| 269 | 269-287 | gaCfgAfaUfaUfgAfuCf cAfaCfaAfdTsdT | 72 | UfUfgUfuGfgAfuCfaUfaUfuCf gUfcdTsdT | 73 |
| 270 | 270-288 | acGfaAfuAfuGfaUfcCf aAfcAfaUfdTsdT | 74 | AfUfuGfuUfgGfaUfcAfuAfuU fcGfudTsdT | 75 | siRNA Sequence with Chemical Modification Info
lower case (n) = 2'-O-Me; Nf = 2'-F; dT = deoxy-T residue; s = phosphorothioate backbone modification; iB = inverted abasic

Example 2. Evaluation of In Vitro Potency of Anti-KRas siRNAs

The anti-KRas siRNAs sequences listed in Table 4 were transfected in two human non-small cell lung cancer (NSCLC) cell lines, H358 (KRas G12C) and H1975 (KRas WT). Each siRNA was formulated with a Lipofectamine RNAiMAX (Life Technologies), according to the manufacturer's "forward transfection" instructions, at a single final concentration of 5 nM. Cells were plated 24 h prior to transfection in duplicate within 24-well tissue culture plates. At 48 h post-transfection, RNA was harvested from cells in all wells using Stratec InviTrap® RNA Cell HTS96 kit. The concentration of each isolated RNA was determined via A260 measurement using a NanoDrop spectrophotometer. RNA samples were reverse transcribed to cDNA using the High Capacity RNA to cDNA Kit (Life Technologies) according to the manufacturer's instructions. cDNA samples were then evaluated by qPCR using KRas-specific probes with results normalized to endogenous β-actin and quantified using the standard $2^{-\Delta\Delta Ct}$ method. KRas mRNA levels were normalized to expression in vehicle controls and are reported in Table 4.

TABLE 4

| siRNA # | sense strand sequence (5'-3') | SEQ ID NO: | antisense strand sequence (5'-3') | SEQ ID NO: | qPCR, H358, 5 nM % Rel KRas mRNA | qPCR, H1975, 5 nM % Rel KRas mRNA |
|---|---|---|---|---|---|---|
| R-1053 | ugAfcUfgAfaUfaUfaAfa CfuUfgUfdTsdT | 48 | AfCfaAfgUfuUfaUfaUfuUf CfaGfuCfadTsdT | 49 | 9.8 | 12.9 |
| R-1057 | aaGfaGfuGfcCfuUfgAfc GfaUfaCfdTsdT | 56 | GfUfaUfcGfuCfaAfgGfc AfcUfcUfudTsdT | 57 | 11.7 | 8.7 |
| R-1058 | agAfgUfgCfcUfuGfaCfg AfuAfcAfdTsdT | 58 | UfGfuAfuCfgUfcAfaGfg CfaCfuCfudTsdT | 59 | 14.4 | 24.9 |
| R-1052 | auGfaCfuGfaAfuAfuAfa AfcUfuGfdTsdT | 46 | CfAfaGfuUfuAfuAfuUfc AfgUfcAfudTsdT | 47 | 14.5 | 19.2 |
| R-1056 | caAfgAfgUfgCfcUfuGfa CfgAfuAfdTsdT | 54 | UfAfuCfgUfcAfaGfgCfa CfuCfuUfgdTsdT | 55 | 15 | 17 |
| R-1060 | gcCfuUfgAfcGfaUfaCfa GfcUfaAfdTsdT | 62 | UfUfaGfcUfgUfaUfcGfu CfaAfgGfcdTsdT | 63 | 18.5 | 36.7 |

TABLE 4-continued

| siRNA # | sense strand sequence (5'-3') | SEQ ID NO: | antisense strand sequence (5'-3') | SEQ ID NO: | qPCR, H358, 5 nM % Rel KRas mRNA | qPCR, H1975, 5 nM % Rel KRas mRNA |
|---|---|---|---|---|---|---|
| R-1063 | caGfcUfaAfuUfcAfgAfa UfcAfuUfdTsdT | 68 | AfAfuGfaUfuCfuGfaAfu UfaGfcUfgdTsdT | 69 | 19.8 | 14.8 |
| R-1062 | ugAfcGfaUfaCfaGfcUfa AfuUfcAfdTsdT | 66 | UfGfaAfuUfaGfcUfgUfa UfcGfuCfadTsdT | 67 | 20 | 14.8 |
| R-1064 | guGfgAfcGfaAfuAfuGfa UfcCfaAfdTsdT | 70 | UfUfgGfaUfcAfuAfuUfc GfuCfcAfcdTsdT | 71 | 22.2 | 33.6 |
| R-1054 | cuUfgUfgGfuAfgUfuGfg AfgCfuGfdTsdT | 50 | CfAfgCfuCfcAfaCfuAfc CfaCfaAfgdTsdT | 51 | 29.4 | 64.6 |
| R-1061 | uuGfaCfgAfuAfcAfgCfu AfaUfuCfdTsdT | 64 | GfAfaUfuAfgCfuGfuAfu CfgUfcAfadTsdT | 65 | 37 | 72.4 |
| R-1059 | ugCfcUfuGfaCfgAfuAfc AfgCfuAfdTsdT | 60 | UfAfgCfuGfuAfuCfgUfc AfaGfgCfadTsdT | 61 | 44.6 | 99.3 |
| R-1065 | gaCfgAfaUfaUfgAfuCfc AfaCfaAfdTsdT | 72 | UfUfgGfuUfgGfaUfcAfuAfa UfuCfgUfcdTsdT | 73 | 46 | 72 |
| R-1055 | ggCfaAfgAfgUfgCfcUfu GfaCfgAfdTsdT | 52 | UfCfgUfcAfaGfgCfaCfu CfuUfgCfcdTsdT | 53 | 52.3 | 90.9 |
| R-1066 | acGfaAfuAfuGfaUfcCfa AfcAfaUfdTsdT | 74 | AfUfuGfuUfgGfaUfcAfu AfuUfcGfudTsdT | 75 | 81.8 | 50.5 | siRNA Sequence with Chemical Modification Info
lower case (n) = 2'-O-Me; Nf = 2'-F; dT = deoxy-T residue; s = phosphorothioate backbone modification; iB = inverted abasic Of the 15 siRNA candidates tested, six achieved ≥80% down-regulation in both cell lines tested. Based upon the results from this initial single-concentration experiment, we selected a total of three candidate siRNAs (ID #183, #227, #237) for multi-concentration testing, to determine $IC_{50}$ values (i.e., the concentration required to reduce KRas expression by 50%), in the two cell lines. Cells were transfected as above at concentrations starting from 5000 pM using serial dilutions. At 48 h post-transfection, RNA was harvested and normalized KRas mRNA levels were quantified as described above. Results are presented in Table 5. All the three siRNA had comparable potency in term of downregulation of KRas mRNA. ID #237 was used to determine if the changes in KRAs mRNA had an effect on cell viability. #237 was also predicted to be able to silence mouse KRas, which was confirmed in Lewis Lung Carcinoma (LLC).

TABLE 5

| siRNA # | sense strand sequence (5'-3') | SEQ ID NO: | antisense strand sequence (5'-3') | SEQ ID NO: | qPCR, H358, IC50, (pM) | qPCR, H1975, IC50, (pM) | qPCR, LLC, IC50, (pM) |
|---|---|---|---|---|---|---|---|
| R-1053 | ugAfcUfgAfaUfaUfaUfa AfaCfuUfgUfdTsdT | 48 | AfCfaAfgUfuUfaUfaUff uCfaGfuCfadTsdT | 49 | 6.1 | 5 | |
| R-1057 | aaGfaGfuGfcCfuUfg AfcGfaUfaCfdTsdT | 56 | GfUfaUfcGfuCfaAfgGf cAfcUfcUfudTsdT | 57 | 2.8 | 1.7 | |
| R-1062 | ugAfcGfaUfaCfaGfc UfaAfuUfcAfdTsdT | 66 | UfGfaAfuUfaGfcUfgUf aUfcGfuCfadTsdT | 67 | 2.7 | 0.3 | 9.9 | siRNA Sequence with Chemical Modification Info
lower case (n) = 2'-O-Me; Nf = 2'-F; dT = deoxy-T residue; s = phosphorothioate backbone modification; iB = inverted abasic Different modification patterns of ID #237 (R-1119, R-1120, and R-1121) were prepared and their effect on KRas mRNA were tested in H358 as described above. Table 6 reports the $IC_{50}$ values and cell viabilities. Modification of R-1121 caused significant activity loss while the other two showed comparable activity to ID #237.

TABLE 6

| siRNA # | sense strand sequence (5'-3') | SEQ ID NO: | antisense strand sequence (5'-3') | SEQ ID NO: | qPCR, H358, IC50, pM | Viability H358, IC50, pM | Viability H441, IC50, pM2 | Viability SW1116, IC50, pM22 |
|---|---|---|---|---|---|---|---|---|
| R-1062 | ugAfcGfaUfaCfaGfcUfaAfuUfcAfdTsdT | 66 | UfGfaAfuUfaGfcUfgUfaUfcGfuCfadTsdT | 67 | 2.7 | 26.9 | | |
| R-1119 | UGACGAUACAGCUAAUUCAdTsdT | 76 | UGAAUUAGCUGUAUCGUCAdTsdT | 77 | 4.3 | 25.4 | | |
| R-1120 | iBugAfcGfaUfaCfaGfcUfaAfuUfcAfusuiB | 78 | UfsGfsasAfuUfaGfcUfgUfaUfcGfuCfausu | 79 | 4.1 | 76.2 | 11.5 | 44 |
| R-1121 | iBugAfcGfaUfaCfaGfcUfaAfuUfcAfusuiB | 80 | usGfsasAfuUfaGfcUfgUfaUfcGfuCfausu | 81 | 37.8 | 750 | | | siRNA Sequence with Chemical Modification Info
lower case (n) = 2'-O-Me; Nf = 2'-F; dT = deoxy-T residue; s = phosphorothioate backbone modification; iB = inverted abasic Knocking down KRas mRNA is known to affect cell viability and proliferation, particularly in cell lines carrying KRas activating mutations, such as H358 (G12C), H441 (G12V), and SW1116 (G12V). 3000 cells were plated in 384-well plates and increasing concentration of siRNA R-1120 in the presence of RNAiMAX were added to the cell culture. At 4 days post transfection, new media and siRNAs with transfection reagent were added to the cell culture plates for H441 and SW1116 cells. After a total of four (H358) or six (H441 and SW1116) days, cell viability was assessed with CellTiter-Blue® (Promega), according to the manufacturer's instructions and is reported in Table 3. Reducing the levels of KRas mRNA had a dramatic effect on cell growth of H358, H441 and SW1116 cells.

As shown in FIG. 1, using a 3D cell culture assay, it was found that H358 cell viability was reduced in a dose-dependent manner by anti-KRAS siRNA (siRNA R-1120) compared to a scrambled siRNA control. 2500 H358 cells were plated in 96-well Ultra-low binding plates (Corning #7007). Increasing concentration of siRNA R-1120 in the presence of RNAiMAX were added to the cell culture. On day 7, cell viability was assessed with CellTiter-Blue® (Promega), according to the manufacturer's instructions.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A polynucleic acid molecule that mediates RNA interference against Kirsten Rat Sarcoma Viral Oncogene Homolog (KRAS), comprising a sense strand and an antisense strand that hybridizes to a KRAS target sequence selected from SEQ ID NOs: 3, 4, 9, and 15, wherein:

the polynucleic acid molecule comprises 100% modification of nucleotides, wherein the sense strand comprises nnN'nN'n at the 5' end, and the antisense strand comprises N'N'nN'nN' at the 5' end, and wherein n is 2'-O'-methyl modified nucleotide and N' is 2'-F modified nucleotide; and the sense strand and the antisense strand are each at least 19, 20, 21, 22, 23, 24, or 25 nucleotides in length.

2. The polynucleic acid molecule of claim 1, wherein the 2' O-Me modified nucleotide comprises locked nucleic acid (LNA) or ethylene nucleic acid (ENA).

3. The polynucleic acid molecule of claim 1, further comprising at least one inverted abasic moiety at at least one terminus.

4. The polynucleic acid molecule of claim 1, wherein the sense strand and the antisense strand are each 19, 20, or 21 nucleotides in length.

5. The polynucleic acid molecule of claim 1, wherein the sense strand or the antisense strand comprises at least 45% 2'-O-methyl modification.

6. The polynucleic acid molecule of claim 1, wherein the sense strand and the antisense strand each independently comprises RNA molecules.

7. The polynucleic acid molecule of claim 1, wherein the sense strand comprises a sequence having at least 80%, 85%, 90%, 95%, 96%, 97%, 98%, 99%, or 100% sequence identity to a sequence selected from SEQ ID NOs: 20-23, 32, 33, 44, 45, 50-53, 62, 63, 74, and 75.

8. The polynucleic acid molecule of claim 1, wherein the antisense strand comprises a sequence having at least 80%, 85%, 90%, 95%, 96%, 97%, 98%, 99%, or 100% sequence identity to a sequence selected from SEQ ID NOs: 20-23, 32, 33, 44, 45, 50-53, 62, 63, 74, and 75.

9. The polynucleic acid molecule of claim 1, wherein the polynucleic acid molecule comprises two contiguous modified T or U residues at the 3' terminus.

10. The polynucleic acid molecule of claim 1, wherein the polynucleic acid molecule comprises at least one inverted abasic moiety.

11. The polynucleic acid molecule of claim 1, wherein the sense strand comprises at least one inverted abasic moiety.

12. The polynucleic acid molecule of claim 11, wherein the at least one inverted abasic moiety is at the 5' terminus of the sense strand.

13. The polynucleic acid molecule of claim 11, wherein the at least one inverted abasic moiety is at the 3' terminus of the sense strand.

14. A pharmaceutical composition comprising:

a) a molecule of claim 1; and b) a pharmaceutically acceptable excipient.

15. The pharmaceutical composition of claim 14, wherein the pharmaceutical composition is formulated as a nanoparticle formulation.

16. The pharmaceutical composition of claim 14, wherein the pharmaceutical composition is formulated for parenteral, oral, intranasal, buccal, rectal, or transdermal administration.

17. A polynucleic acid molecule that mediates RNA interference against Kirsten Rat Sarcoma Viral Oncogene Homolog (KRAS), comprising a sense strand and an antisense strand that hybridizes to a KRAS target sequence selected from SEQ ID NOs: 3, 4, 9, and 15, wherein:

the polynucleic acid molecule comprises 100% modification of nucleotides, wherein the sense strand comprises nnN'nN'n at the 5' end, and the antisense strand comprises N'N'nN'nN' at the 5' end, and wherein n is 2'-O'-methyl modified nucleotide and N' is 2'-F modified nucleotide;

the sense strand comprises an inverted abasic moiety at the 3' terminus and the 5' terminus of the sense strand; and the polynucleic acid molecule comprises at least one phosphorodithioate linkages at the 3' terminus of the sense strand and the antisense strand.

* * * * *